(12) United States Patent
Joly et al.

(10) Patent No.: US 10,370,322 B2
(45) Date of Patent: *Aug. 6, 2019

(54) ADDITION-FRAGMENTATION AGENTS

(71) Applicant: 3M INNOVATIVE PROPERTIES COMPANY, St. Paul, MN (US)

(72) Inventors: Guy D. Joly, Shoreview, MN (US); Larry R. Krepski, White Bear Lake, MN (US); Ann R. Fornof, Austin, TX (US); Serkan Yurt, St. Paul, MN (US); Babu N. Gaddam, Woodbury, MN (US); Ahmed S. Abuelyaman, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 149 days.

This patent is subject to a terminal disclaimer.

(21) Appl. No.: 15/410,919

(22) Filed: Jan. 20, 2017

(65) Prior Publication Data

US 2017/0210693 A1 Jul. 27, 2017

Related U.S. Application Data

(63) Continuation-in-part of application No. 13/169,306, filed on Jun. 27, 2011, now abandoned.

(60) Provisional application No. 61/442,980, filed on Feb. 15, 2011.

(51) Int. Cl.
| | | |
|---|---|---|
| C09D 133/00 | (2006.01) | |
| C08L 33/00 | (2006.01) | |
| C07C 67/26 | (2006.01) | |
| C07C 269/02 | (2006.01) | |
| C07C 67/14 | (2006.01) | |
| C08F 220/68 | (2006.01) | |
| C09J 133/08 | (2006.01) | |
| C09J 5/00 | (2006.01) | |
| C07C 271/16 | (2006.01) | |
| C07C 69/593 | (2006.01) | |
| C08K 3/22 | (2006.01) | |
| C08K 3/36 | (2006.01) | |
| C09D 133/08 | (2006.01) | |
| C08K 5/11 | (2006.01) | |
| C08K 5/12 | (2006.01) | |
| C08K 5/205 | (2006.01) | |
| C08L 33/10 | (2006.01) | |

(52) U.S. Cl.
CPC ............ *C07C 67/26* (2013.01); *C07C 67/14* (2013.01); *C07C 69/593* (2013.01); *C07C 269/02* (2013.01); *C07C 271/16* (2013.01); *C08F 220/68* (2013.01); *C08K 3/22* (2013.01); *C08K 3/36* (2013.01); *C08K 5/11* (2013.01); *C08K 5/12* (2013.01); *C08K 5/205* (2013.01); *C09D 133/08* (2013.01); *C09J 5/00* (2013.01); *C09J 133/08* (2013.01); *C08L 33/10* (2013.01); *C09J 2433/00* (2013.01)

(58) Field of Classification Search
CPC ..... C09D 133/10; C09D 133/12; C08L 33/10; C08L 33/12
See application file for complete search history.

(56) References Cited

U.S. PATENT DOCUMENTS

| | | | |
|---|---|---|---|
| 3,660,145 | A | 5/1972 | Johnson |
| 3,910,992 | A | 10/1975 | Skillicorn |
| 4,119,640 | A | 10/1978 | Hodakowski |
| 4,184,992 | A | 1/1980 | Hosaka |
| 4,260,701 | A | 4/1981 | Lee, Jr. |
| 4,503,169 | A | 3/1985 | Randklev |
| 4,547,323 | A | 10/1985 | Carlson |
| 4,608,423 | A | 8/1986 | Abbey |
| 4,621,131 | A | 11/1986 | Lin |
| 4,877,838 | A | 10/1989 | Toman |
| 4,886,861 | A | 12/1989 | Janowicz |

(Continued)

FOREIGN PATENT DOCUMENTS

WO WO 2009/091551 7/2009

OTHER PUBLICATIONS

Abbey, et al., "Synthesis and Copolymerization Behavior of Methacrylate Dimers," Journal of Polymer Science, Part A: Polymer Chemistry, vol. 31, pp. 3417-3424, (1993).
Enikolopyan, et al., "Catalyzed Chain Transfer to Monomer in Free Radical Polymerization," Journal of Polymer Science: Polymer Chemistry Edition, vol. 19, pp. 879-889, 1981.
Gridnev, et al., "Catalytic Chain Transfer in Free-Radical Polymerizations," American Chemical Society, Chemical Reviews, vol. 101, No. 12, pp. 3611-3659, 2001.

(Continued)

*Primary Examiner* — Rip A Lee

(57) ABSTRACT

Addition-fragmentation agents of the formula are disclosed:

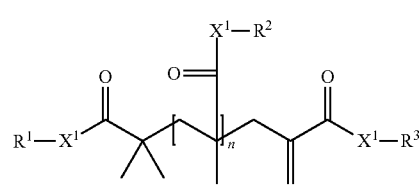

wherein
$R^1$, $R^2$ and $R^3$ are each independently Z-Q-, a (hetero)alkyl group or a (hetero)aryl group with the proviso that at least one of $R^1$, $R^2$ and $R^3$ is $Z_m$-Q-,
Q is a linking group have a valence of m+1;
Z is an ethylenically unsaturated polymerizable group,
m is 1 to 6;
each $X^1$ is independently —O— or —$NR^4$—, where $R^4$ is H or $C_1$-$C_4$ alkyl, and
n is 0 or 1.

19 Claims, No Drawings

(56) References Cited

U.S. PATENT DOCUMENTS

| | | | |
|---|---|---|---|
| 5,242,996 | A | 9/1993 | Yamada |
| 5,324,879 | A | 6/1994 | Hawthorne |
| 5,371,151 | A | 12/1994 | Berge |
| 5,767,211 | A | 6/1998 | Guan |
| 5,773,543 | A | 6/1998 | Rizzardo |
| 6,184,339 | B1 | 2/2001 | Stansbury |
| 6,265,133 | B1 | 7/2001 | Takahashi |
| 6,316,519 | B1 * | 11/2001 | Berge ............ C08F 2/38 522/150 |
| 6,710,127 | B2 | 3/2004 | Haubennestel |
| 6,730,156 | B1 | 5/2004 | Windisch et al. |
| 7,090,721 | B2 | 8/2006 | Craig et al. |
| 7,090,722 | B2 | 8/2006 | Budd et al. |
| 7,156,911 | B2 | 1/2007 | Kangas et al. |
| 7,385,016 | B2 | 6/2008 | Lachowicz |
| 7,649,029 | B2 | 1/2010 | Kolb et al. |
| 7,943,680 | B2 | 5/2011 | Bowman et al. |
| 8,080,623 | B2 | 12/2011 | Kojima |
| 8,980,969 | B2 * | 3/2015 | Joly ............ C08F 2/38 522/33 |
| 9,056,043 | B2 * | 6/2015 | Joly ............ A61K 6/083 |
| 9,403,966 | B2 * | 8/2016 | Joly ............ C07C 69/593 |
| 2005/0008967 | A1 | 1/2005 | Kunita |
| 2005/0261412 | A1 | 11/2005 | Bandou |
| 2006/0009574 | A1 | 1/2006 | Aert |
| 2008/0015315 | A1 | 1/2008 | Chang |
| 2008/0076848 | A1 | 3/2008 | Jin et al. |
| 2008/0076853 | A1 | 3/2008 | Jin et al. |
| 2010/0021869 | A1 | 1/2010 | Abuelyaman |
| 2012/0208965 | A1 | 8/2012 | Joly |
| 2013/0012614 | A1 | 1/2013 | Abuelyaman |
| 2013/0316307 | A1 | 11/2013 | Joly |
| 2014/0206788 | A1 | 7/2014 | Joly |

OTHER PUBLICATIONS

Guan, et al., "Control of Polymer Architecture by a Special Chain Transfer Catalyst," C. Polym. Mater. Sci. Eng., vol. 79, p. 7-8, 1998.

Hutson, et al., "Chain Transfer Activity of ω-Unsaturated Methacrylic Oligomers in Polymerizations of Methacrylic Monomers," Macromolecules, vol. 37, pp. 4441-4452, 2004.

Kloxin, et al., "Stress Relaxation via Addition-Fragmentation Chain Transfer in a Thiolene Photopolymerization," Macromolecules, vol. 42, pp. 2551-2556, 2009.

Moad, et al., "Chain Transfer Activity of ω-Unsaturated Methyl Methacrylate Oligomers," Macromolecules, vol. 29, pp. 7717-7726, 1996.

Watts, et al., "Determination of polymerization shrinkage kinetics in visible-light-cured materials; methods development," Dental Materials, pp. 281-287, Oct. 1991.

PCT International Search Report, PCT/US2012/023475, dated Mar. 13, 2012.

* cited by examiner

ADDITION-FRAGMENTATION AGENTS

CROSS REFERENCE TO RELATED APPLICATION

This application is a continuation-in-part of U.S. application Ser. No. 13/169,306, filed Jun. 27, 2011, which claims the benefit of U.S. Provisional Patent Application No. 61/442,980, filed Feb. 15, 2011, the disclosure of which is incorporated by reference herein in its entirety.

BACKGROUND

The present disclosure provides novel addition-fragmentation agents for use in low-stress polymerizable compositions. Free-radical polymerization is typically accompanied by a reduction in volume as monomers are converted to polymer. The volumetric shrinkage produces stress in the cured composition, leading to a microcracks and deformation. Stress transferred to an interface between the cured composition and a substrate can cause failure in adhesion and can affect the durability of the cured composition.

The crosslinking agents of this disclosure provide stress relief by including labile crosslinks that can cleave and reform during the polymerization process. Crosslink cleavage may provide a mechanism to allow for network reorganization, relieve polymerization stress, and prevent the development of high stress regions. The instant crosslinking agent may further provide stress relief by delaying the gel point, the point at which the polymerizable composition transitions from a viscous material to an elastic solid. The longer the polymerizable mixture remains viscous, the more time available during which material flow can act to alleviate stress during the polymerization process.

The addition-fragmentation crosslinking agents provide novel stress-reducing crosslinking agents that have application in dental restoratives, thin films, hardcoats, composites, adhesives, and other uses subject to stress reduction. In addition, the addition-fragmentation process of crosslinking results in a chain-transfer event that provides novel polymers that may be further functionalized.

SUMMARY

The present disclosure provides addition-fragmentation agents of the formula:

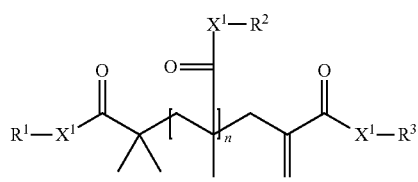

wherein
$R^1$, $R^2$ and $R^3$ are each independently $Z_m$-Q-, a (hetero)alkyl group or a (hetero)aryl group with the proviso that at least one of $R^1$, $R^2$ and $R^3$ is $Z_m$-Q-,
Q is a linking group have a valence of m+1;
Z is an ethylenically unsaturated polymerizable group,
m is 1 to 6, preferably 1 to 2;
each $X^1$ is independently —O— or —$NR^4$—, where $R^4$ is H or $C_1$-$C_4$ alkyl, and
n is 0 or 1.

The addition-fragmentation agents of Formula I may be added to polymerizable monomer mixtures to reduce the polymerization-induced stresses. In embodiments where Z is ≥2, the agents further function as addition-fragmentation crosslinking agents, where the crosslinks are labile. This disclosure further provides a method of preparing the addition-fragmentation agents of formula I, as further disclosed herein.

This disclosure further provides a curable composition comprising the addition-fragmentation agent and one or more free-radically polymerizable monomers, the addition-fragmentation agent providing a reduction in shrinkage and stress of the resultant polymers. The addition-fragmentation agents act as chain-transfer agents via an addition-fragmentation process whereby the crosslinks are labile during polymerization and continuously cleave and reform, providing a reduction in polymerization-based stress.

As used herein:

"acryloyl" is used in a generic sense and mean not only derivatives of acrylic acid, but also amine, and alcohol derivatives, respectively;

"(meth)acryloyl" includes both acryloyl and methacryloyl groups; i.e. is inclusive of both esters and amides.

"curable" means that a coatable material can be transformed into a solid, substantially non-flowing material by means of free-radical polymerization, chemical cross linking, radiation crosslinking, or the like.

"alkyl" includes straight-chained, branched, and cyclic alkyl groups and includes both unsubstituted and substituted alkyl groups. Unless otherwise indicated, the alkyl groups typically contain from 1 to 20 carbon atoms. Examples of "alkyl" as used herein include, but are not limited to, methyl, ethyl, n-propyl, n-butyl, n-pentyl, isobutyl, t-butyl, isopropyl, n-octyl, n-heptyl, ethylhexyl, cyclopentyl, cyclohexyl, cycloheptyl, adamantyl, and norbornyl, and the like. Unless otherwise noted, alkyl groups may be mono- or polyvalent, i.e monovalent alkyl or polyvalent alkylene.

"heteroalkyl" includes both straight-chained, branched, and cyclic alkyl groups with one or more heteroatoms independently selected from S, O, and N with both unsubstituted and substituted alkyl groups. Unless otherwise indicated, the heteroalkyl groups typically contain from 1 to 20 carbon atoms. "Heteroalkyl" is a subset of "hydrocarbyl containing one or more S, N, O, P, or Si atoms" described below. Examples of "heteroalkyl" as used herein include, but are not limited to, methoxy, ethoxy, propoxy, 3,6-dioxaheptyl, 3-(trimethylsilyl)-propyl, 4-dimethylaminobutyl, and the like. Unless otherwise noted, heteroalkyl groups may be mono- or polyvalent, i.e. monovalent heteroalkyl or polyvalent heteroalkylene.

"aryl" is an aromatic group containing 6-18 ring atoms and can contain optional fused rings, which may be saturated, unsaturated, or aromatic. Examples of an aryl groups include phenyl, naphthyl, biphenyl, phenanthryl, and anthracyl. Heteroaryl is aryl containing 1-3 heteroatoms such as nitrogen, oxygen, or sulfur and can contain fused rings. Some examples of heteroaryl groups are pyridyl, furanyl, pyrrolyl, thienyl, thiazolyl, oxazolyl, imidazolyl, indolyl, benzofuranyl, and benzthiazolyl. Unless otherwise noted, aryl and heteroaryl groups may be mono- or polyvalent, i.e. monovalent aryl or polyvalent arylene.

"(hetero)hydrocarbyl" is inclusive of hydrocarbyl alkyl and aryl groups, and heterohydrocarbyl heteroalkyl and heteroaryl groups, the later comprising one or more catenary oxygen heteroatoms such as ether or amino groups. Heterohydrocarbyl may optionally contain one or more catenary (in-chain) functional groups including ester, amide, urea, urethane, and carbonate functional groups. Unless otherwise indicated, the non-polymeric (hetero)hydrocarbyl groups typically contain from 1 to 60 carbon atoms. Some examples of such heterohydrocarbyls as used herein include, but are not limited to, methoxy, ethoxy, propoxy, 4-diphenylaminobutyl, 2-(2'-phenoxyethoxy)ethyl, 3,6-dioxaheptyl, 3,6-dioxahexyl-6-phenyl, in addition to those described for "alkyl", "heteroalkyl", "aryl", and "heteroaryl" supra.

DETAILED DESCRIPTION

The present disclosure provides addition-fragmentation agents of the Formula I, supra. The ethylenically unsaturated moiety, Z, of the monomer may include, but is not limited to the following structures, including (meth)acryloyl, vinyl, styrenic and ethynyl, that are more fully described in reference to the preparation of the compounds below.

It is believed that the addition-fragmentation agent follows an addition fragmentation pathway as shown in the following Scheme 1. In this scheme the crosslinking agent of Formula I is shown, where n is 0. In the step 1, a free radical species P adds to the crosslinking agent. The crosslinking agent then fragments as shown in step 2 to form the stable α-carbonyl tertiary radical and the α,β-unsaturated ester bearing the residue of the free radical species P•. This α,β-unsaturated ester can undergo radical addition as shown in step 5. The radical addition may be initiated by an initiator or a polymer radical.

Concurrently the α-carbonyl tertiary radical can initiate polymerization of monomer as shown in step 3. For purposes of illustration, a methacrylate monomer is illustrated. On monomer addition, a methacrylate terminated radical intermediate is produced. In the presence of the crosslinking agent of Formula 1 (as shown in step 4) both addition, and fragmentation, yielding a tertiary radical, occurs.

Scheme 1.

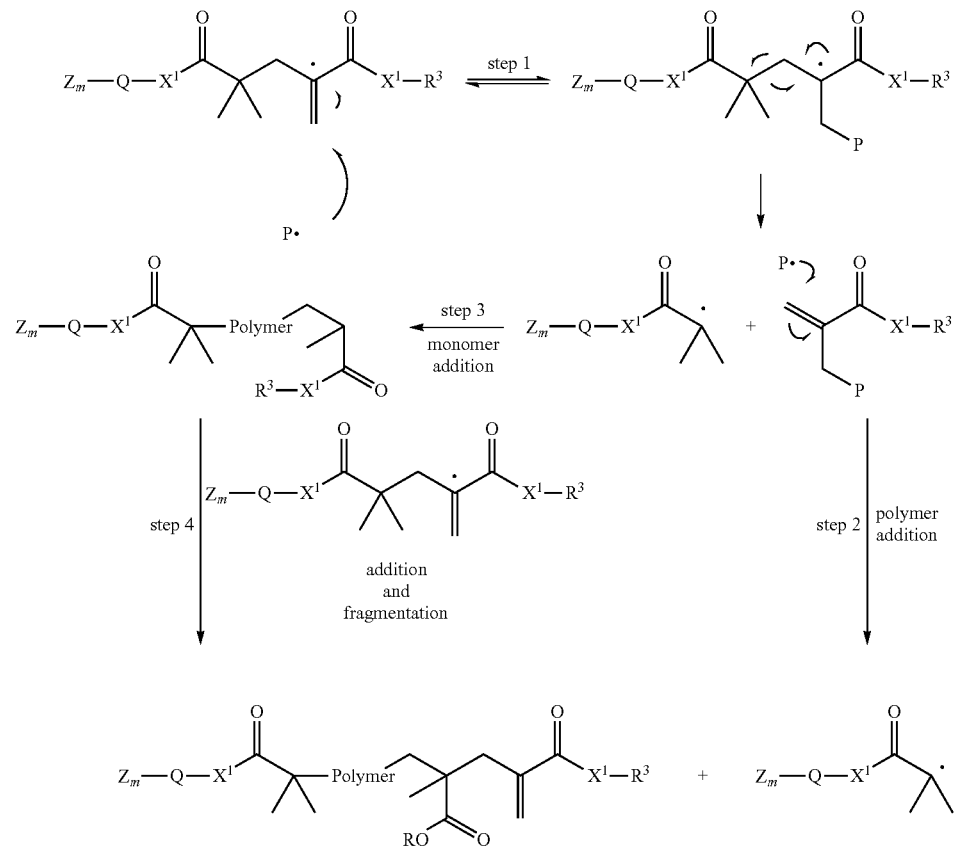

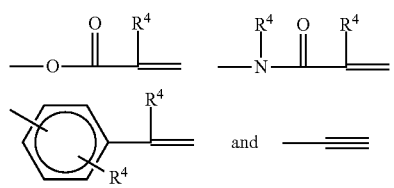

wherein $R^4$ is H or $C_1$-$C_4$ alkyl

As shown in the following Scheme 2, the addition-fragmentation crosslinking agents provide multiple potential mechanisms for stress relief. A simplified methacrylate polymer is shown crosslinked by the two "Z" groups of the addition fragmentation crosslinking agent. The bonds between the ethylenically unsaturated Z groups will form labile crosslinks. Fragmentation of the addition-fragmentation crosslinking agent provides a mechanism for crosslink cleavage. The cleavage of labile crosslinks may allow the polymeric network to relax or reorganize, especially in high stress regions, providing a potential mechanism for stress relief.

Scheme 2
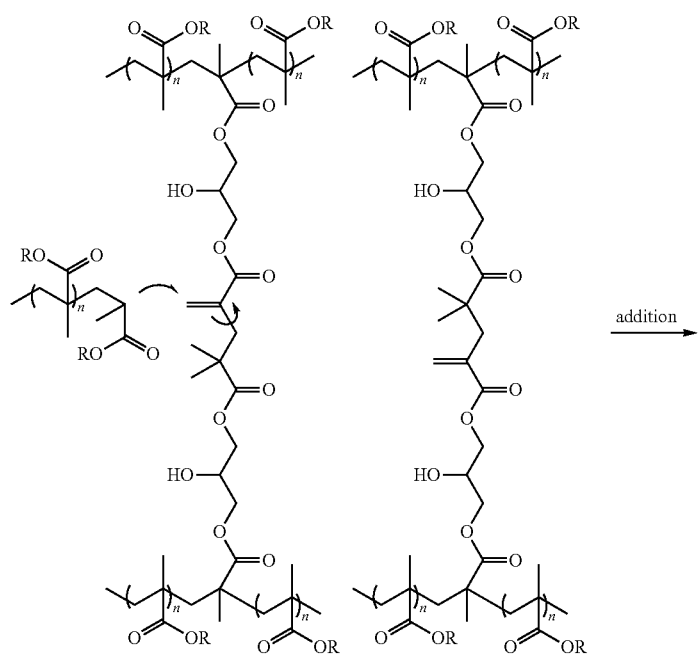
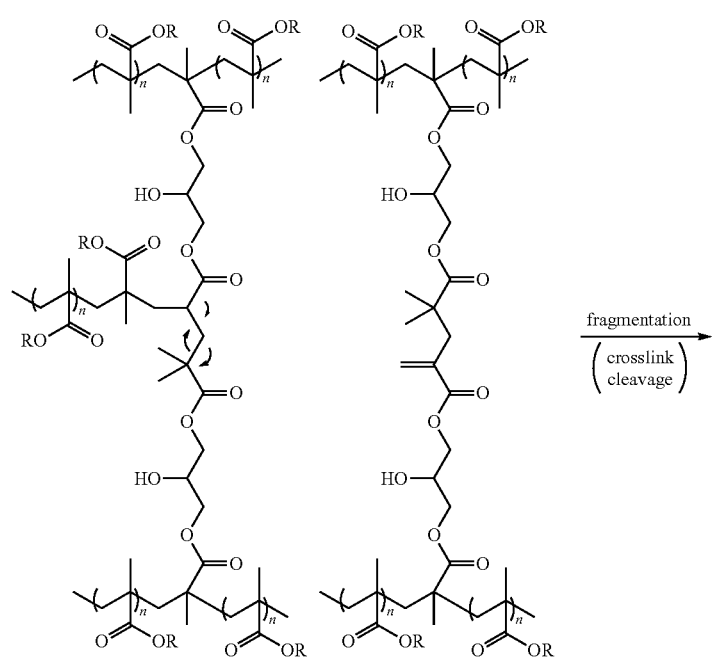

-continued

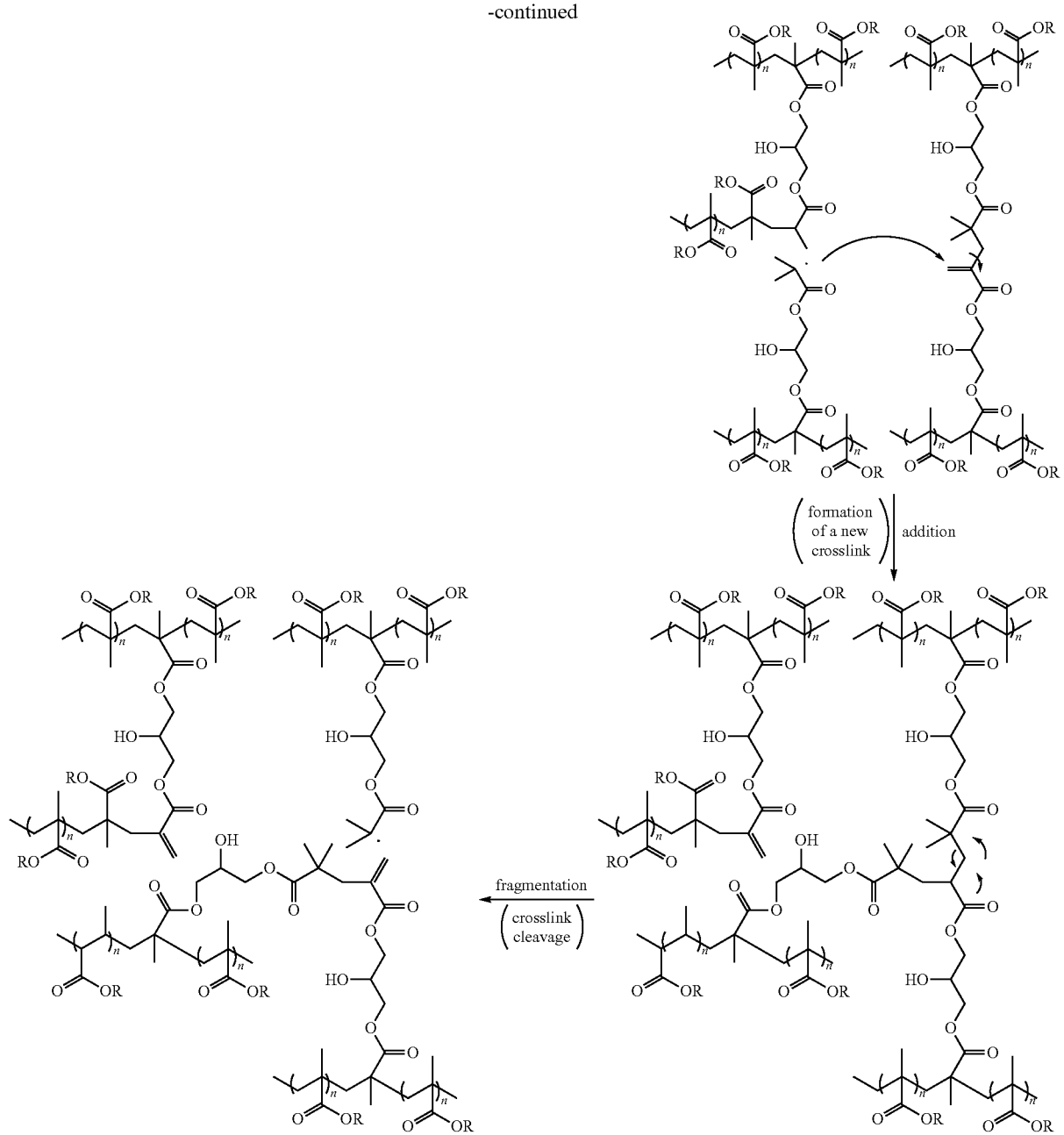

Stress relief could also be a result of attenuated reaction rates (slower cure rates) in the presence of addition-fragmentation materials. The addition of a radical to the addition-fragmentation crosslinking agent generates a potentially long-lived, tertiary radical (the product of step 1, Scheme 1). This long-lived radical intermediate can revert back to starting materials, add to monomer, or fragment. If fragmentation, retro-addition and monomer addition are slow relative to addition, the intermediate tertiary radical will be relatively long-lived. This long-lived radical intermediate will then act as a radical reservoir, slowing down the overall polymerization process. Attenuated cure rates could serve to delay the transition of a material from a viscous material to an elastic solid, delaying the gel point. Post-gel shrinkage is a major component in stress development; therefore, delaying the gel point even slightly may lead to stress relief by allowing additional time for material to flow during the curing process. Therefore, even compounds of Formula I, having a single Z group, may be used to reduce polymerization stress.

The compounds of Formula I may be prepared from (meth)acrylate dimers and trimers by substitution, displacement or condensation reactions. The starting (meth)acrylate dimers and trimers may be prepared by free radical addition of a (meth)acryloyl monomer in the presence of a free radical initiator and a cobalt (II) complex catalyst using the process of U.S. Pat. No. 4,547,323 (Carlson), incorporated herein by reference. Alternatively, the (meth)acryloyl dimers and trimers may be prepared using a cobalt chelate complex using the processes of U.S. Pat. No. 4,886,861 (Janowicz) or U.S. Pat. No. 5,324,879 (Hawthorne), incorporated herein by reference. In either process, the reaction mixture can contain a complex mixture of dimers, trimers, higher oligomers and polymers and the desired dimer or trimer can be separated from the mixture by distillation.

With reference to Formula I, the requisite ethylenically unsaturated "Z" group may be incorporated into the (meth) acryloyl dimer or trimer by means including addition, condensation, substitution and displacement reaction. In general, one or more of the acyl groups of the (meth)acryloyl dimer or trimer is provided with the $Z\text{-}Q\text{-}X^1$— group of Formula I.

More specifically, a (meth)acryloyl compound of the formula:

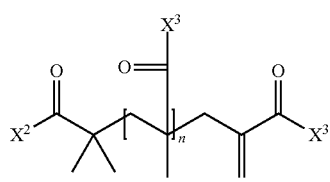

II wherein $X^2$ comprises an electrophilic or nucleophilic functional group,
$X^3$ is $X^2$, $X^1$—$R^2$ or $X^1$—$R^3$, and
n is 0 or 1;
is reacted with a co-reactive compound of the formula:

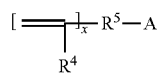

III wherein
A is a functional group that is co-reactive with functional group $X^2$, $R^4$ is hydrogen, a $C_1$ to $C_4$ alkyl group, $R^5$ is a single bond or a di- or trivalent (hetero)hydrocarbyl linking group that joins the ethylenically unsaturated group to reactive functional group A, and x is 1 or 2.

More specifically, $R^5$ is a single bond or a di- or trivalent linking group that joins an ethylenically unsaturated group to co-reactive functional group A and preferably contains up to 34, preferably up to 18, more preferably up to 10, carbon and, optionally, oxygen and nitrogen atoms, optional catenary ester, amide, urea, urethane and carbonate groups. When $R^5$ is not a single bond, is may be selected from —O—, —S—, —NR$^4$—, —SO$_2$—, —PO$_2$—, —CO—, —OCO—, —NR$^4$—CO—, NR$^4$—CO—O—, NR$^4$—CO—NR$^4$—, —R$^6$— and combinations thereof, such as —CO—O—R$^6$—, —CO—NR$^4$—R$^6$—, and —R$^6$—CO—O—R$^6$—.
wherein each $R^4$ is hydrogen, a $C_1$ to $C_4$ alkyl group, or aryl group, each $R^6$ is an alkylene group having 1 to 6 carbon atoms, a 5- or 6-membered cycloalkylene group having 5 to 10 carbon atoms, or a divalent aromatic group having 6 to 16 carbon atoms; and A is a reactive functional group capable of reacting with a co-reactive functional group for the incorporation of a free-radically polymerizable functional "Z" group.

It will be understood that reaction between the $X^2$ group of Formula II and the A group of Formula III will form the $Z_m\text{-}Q\text{-}X^1$— moiety of Formula I, therefore Q may be defined as —$R^5$-A*-$X^{2*}$—, where A*-$X^{2*}$— is the bond formed between A and $X^2$, as described supra. Therefore Q may be defined as single bond or a divalent linking (hetero)hydrocarbyl group. More particularly, Q a single bond or a divalent linking group that joins an ethylenically unsaturated group to co-reactive functional group A and preferably contains up to 34, preferably up to 18, more preferably up to 10, carbon and, optionally, oxygen and nitrogen atoms, optional catenary ester, amide, urea, urethane and carbonate groups. When Q is not a single bond, it may be selected from —O—, —S—, —NR$^4$—, —SO$_2$—, —PO$_2$—, —CO—, —OCO—, —R$^6$— and combinations thereof, such as NR$^4$—CO—NR$^4$—, NR$^4$—CO—O—, NR$^4$—CO—NR$^4$—CO—O—R$^6$—, —CO—NR$^4$—R$^6$—, and —R$^6$—CO—O—R$^6$—, —O—R$^6$—, —S—R$^6$—, —NR$^4$—R$^6$—, —SO$_2$—R$^6$—, —PO$_2$—R$^6$—, —CO—R$^6$—, —OCO—R$^6$—, —NR$^4$—CO—R$^6$—, NR$^4$—R$^6$—CO—O—, NR$^4$—CO—NR$^4$—, —R$^6$—, with the proviso that Q-Z does not contain peroxidic linkages, i.e. O—O, N—O, S—O, N—N, N—S bonds.

wherein each $R^4$ is hydrogen, a $C_1$ to $C_4$ alkyl group, or aryl group, each $R^6$ is an alkylene group having 1 to 6 carbon atoms, a 5- or 6-membered cycloalkylene group having 5 to 10 carbon atoms, or a divalent arylene group having 6 to 16 carbon atoms.

In reference to Formula I, particularly useful $R^1$—$X^1$— groups (and optionally $R^2$—$X^2$— groups) include H$_2$C=C(CH$_3$)C(O)—O—CH$_2$—CH(OH)—CH$_2$—O—, H$_2$C=C(CH$_3$)C(O)—O—CH$_2$—CH(O—(O)C(CH$_3$)=CH$_2$)—CH$_2$—O—, H$_2$C=C(CH$_3$)C(O)—O—CH(CH$_2$OPh)-CH$_2$—O—, H$_2$C=C(CH$_3$)C(O)—O—CH$_2$CH$_2$—N(H)—C(O)—O—CH(CH$_2$OPh)-CH$_2$—O—., H$_2$C=C(CH$_3$)C(O)—O—CH$_2$—CH(O—(O)C—N(H)—CH$_2$CH$_2$—O—(O)C(CH$_3$)C=CH$_2$)—CH$_2$—O—, H$_2$C=C(H)C(O)—O—(CH$_2$)$_4$—O—CH$_2$—CH(OH)—CH$_2$—O—, H$_2$C=C(CH$_3$)C(O)—O—CH$_2$—CH(O—(O)C—N(H)—CH$_2$CH$_2$—O—(O)C(CH$_3$)C=CH$_2$)—CH$_2$—O—, CH$_3$—(CH$_2$)$_7$—CH(O—(O)C—N(H)—CH$_2$CH$_2$—O—(O)C(CH$_3$)C=CH$_2$)—CH$_2$—O—, H$_2$C=C(H)C(O)—O—(CH$_2$)$_4$—O—CH$_2$—CH(—O—(O)C(H)=CH$_2$)—CH$_2$—O— and H$_2$C=C(H)C(O)—O—CH$_2$—CH(OH)—CH$_2$—O—. H$_2$C=C(H)C(O)—O—(CH$_2$)$_4$—O—CH$_2$—CH(—O—(O)C(H)=CH$_2$)—CH$_2$—O—, and CH$_3$—(CH$_2$)$_7$—CH(O—(O)C—N(H)—CH$_2$CH$_2$—O—(O)C(CH$_3$)C=CH$_2$)—CH$_2$—O—
Preferably the $R^1$—$X^1$— groups and $R^2$—$X^2$ groups are the same.

With respect to the compound of formula II, the carboxylic acids ($X^2$, $X^3$=OH) may first be reacted with an epoxy or aziridinyl compound, and subsequently (meth)acrylated, or, reacted with an aziridine- or epoxy-functional (meth) acrylate, as illustrated in Scheme III. It will be understood that different isomers from those depicted may result from the ring-opening. In Scheme III, transverse methyl groups are indicated as attached to either of the adjacent carbon atoms. Note also the reaction with methylaziridine may result in a mixture of acrylate and acrylamide products.

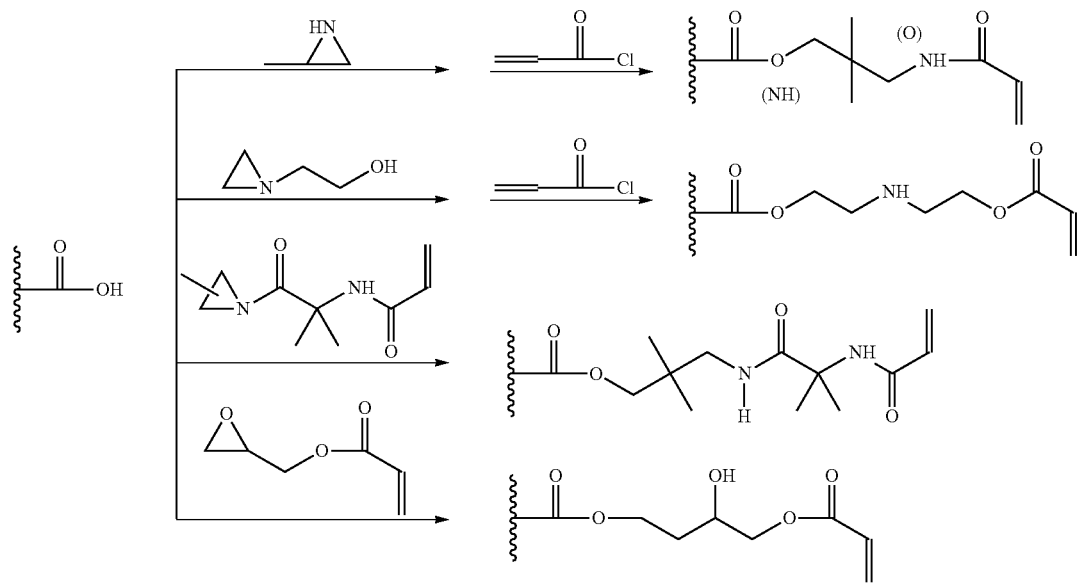

Useful reactive (and co-reactive) functional groups include hydroxyl, secondary amino, oxazolinyl, oxazolonyl, acetylacetonate, carboxyl, isocyanato, epoxy, aziridinyl, acyl halide, and cyclic anhydride groups. Where the reactive functional group of the (meth)acrylate dimer/trimer is an isocyanato functional group, the co-reactive functional group preferably comprises a secondary amino or hydroxyl group. Where the reactive functional group comprises a hydroxyl group, the co-reactive functional group preferably comprises a carboxyl, ester, acyl halide, isocyanato, epoxy, anhydride, azlactonyl or oxazolinyl group. Where the pendent reactive functional group comprises a carboxyl group, the co-reactive functional group preferably comprises a hydroxyl, amino, epoxy, isocyanate, or oxazolinyl group. Most generally, the reaction is between a nucleophilic and electrophilic functional groups.

Representative examples of useful compounds of Formula III having co-reactive functional groups include hydroxyalkyl (meth)acrylates such as 2-hydroxyethyl (meth)acrylate, 3-hydroxypropyl (meth)acrylate, 2, 3-dihydroxypropyl (meth)acrylate, 4-hydroxybutyl (meth)acrylate and 2-(2-hydroxyethoxy)ethyl (meth)acrylate; aminoalkyl (meth)acrylates such as 3-aminopropyl (meth)acrylate and 4-aminostyrene; oxazolinyl compounds such as 2-ethenyl-1,3-oxazolin-5-one, 2-vinyl-4,4-dimethyl-1,3-oxazolin-5-one, 2-isopropenyl-4,4-dimethyl-1,3-oxazolin-5-one and 2-propenyl-4,4-dimethyl-1,3-oxazolin-5-one; carboxy-substituted compounds such as (meth)acrylic acid and 4-carboxybenzyl (meth)acrylate; isocyanato-substituted compounds such as isocyanatoethyl (meth)acrylate and 4-isocyanatocyclohexyl (meth)acrylate; epoxy-substituted compounds such as glycidyl (meth)acrylate; aziridinyl-substituted compounds such as N-acryloylaziridine and 1-(2-propenyl)-aziridine; and acryloyl halides such as (meth) acryloyl chloride.

Representative hydroxyl group-substituted functional compounds of Formula III include the hydroxyalkyl acrylates and hydroxyalkyl acrylamides such as 2-hydroxyethyl (meth)acrylate, 4-hydroxybutyl (meth)acrylate, 2-hydroxypropyl (meth)acrylate, 3-chloro-2-hydroxypropylmethyl (meth)acrylate, 2-hydroxyethyl (meth)acrylamide, 4-hydroxycyclohexyl (meth)acrylate, 3-acryloyloxyphenol, 2-(4-(meth)acryloyloxyphenyl)-2-(4-hydroxyphenyl)propane (also called bisphenol A monoacrylate), 2-propyn-1-ol, and 3-butyn-1-ol.

Representative amino group-substituted functional compounds of Formula III include 2-methyl aminoethyl (meth)acrylate, 3-aminopropyl (meth)acrylate, 4-aminocyclohexyl (meth)acrylate, N-(3-aminophenyl) (meth)acrylamide, N-(meth)acryloylethylenediamine, and 4-aminophenyl-4-acrylamidophenylsulfone.

Representative azlactone group-substituted functional compounds of Formula III include: 2-ethenyl-1,3-oxazolin-5-one; 2-ethenyl-4-methyl-1,3-oxazolin-5-one; 2-isopropenyl-1,3-oxazolin-5-one; 2-isopropenyl-4-methyl-1,3-oxazolin-5-one; 2-ethenyl-4,4-dimethyl-1,3-oxazolin-5-one; 2-isopropenyl-4,4-dimethyl-1,3-oxazolin-5-one; 2-ethenyl-4-methyl-4-ethyl-1,3-oxazolin-5-one; 2-isopropenyl-3-oxa-1-aza[4.5]spirodec-1-ene-4-one; 2-ethenyl-5,6-dihydro-4H-1,3-oxazin-6-one; 2-ethenyl-4,5,6,7-tetrahydro-1,3-oxazepin-7-one; 2-isopropenyl-5,6-dihydro-5,5-di(2-methylphenyl)-4H-1,3-oxazin-6-one; 2-acryloyloxy-1,3-oxazolin-5-one; 2-(2-acryloyloxy)ethyl-4,4-dimethyl-1,3-oxazolin-5-one; 2-ethenyl-4,5-dihydro-6H-1,3-oxazin-6-one; and 2-ethenyl-4,5-dihydro-4,4-dimethyl-6H-1,3-oxazin-6-one.

Representative oxazolinyl group-substituted functional compounds of Formula III include 2-vinyl-2-oxazoline, 2-isopropenyl-2-oxazoline, 2-(5-hexenyl)-2-oxazoline, 2-acryloxy-2-oxazoline, 2-(4-acryloxyphenyl)-2-oxazoline, and 2-methacryloxy-2-oxazoline.

Representative acetoacetyl group-substituted functional compounds of Formula III include 2-(acetoacetoxy)ethyl acrylate.

Representative carboxyl group-substituted functional compounds of Formula III include (meth)acrylic acid, 3-(meth)acryloyloxy-propionic acid, 4-(meth)acryloyloxy-butyric acid, 2-(meth)acryloyloxy-benzoic acid, 3-(meth)acryloyloxy-5-methyl benzoic acid, 4-(meth)acryloyloxymethyl-benzoic acid, phthalic acid mono-[2-(meth)acryloyloxy-ethyl]ester, 2-butynoic acid, and 4-pentynoic acid.

Representative isocyanate group-substituted functional compounds of Formula III include 2-isocyanatoethyl (meth)acrylate, 3-isocyanatopropyl (meth)acrylate, 4-isocyanatocyclohexyl (meth)acrylate, 4-isocyanatostyrene, 2-methyl-2-propenoyl isocyanate, 4-(2-(meth)acryloyloxyethoxycarbonylamino) phenylisocyanate, allyl 2-isocyanatoethylether, and 3-isocyanato-1-propene.

Representative epoxy group-substituted functional compounds of Formula III include glycidyl (meth)acrylate, thioglycidyl (meth)acrylate, 3-(2,3-epoxypropoxy)phenyl (meth)acrylate, 2-[4-(2,3-epoxypropoxy)phenyl]-2-(4-(meth)acryloyloxy-phenyl)propane, 4-(2,3-epoxypropoxy) cyclohexyl (meth)acrylate, 2,3-epoxycyclohexyl (meth) acrylate, and 3,4-epoxycyclohexyl (meth)acrylate.

Representative aziridinyl group-substituted functional compounds of Formula III include N-(meth)acryloylaziridine, 2-(1-aziridinyl)ethyl (meth)acrylate, 4-(1-aziridinyl) butyl acrylate, 2-[2-(1-aziridinyl)ethoxy]ethyl (meth)acrylate, 2-[2-(1-aziridinyl)ethoxycarbonylamino]ethyl (meth) acrylate, 12-[2-(2,2,3,3-tetramethyl-1-aziridinyl) ethoxycarbonylamino] dodecyl (meth)acrylate, and 1-(2-propenyl)aziridine.

Representative acyl halide group-substituted functional compounds of Formula III include (meth)acryloyl chloride, α-chloro(meth)acryloyl chloride, (meth)acryloyloxyacetyl chloride, 5-hexenoyl chloride, 2-(acryloyloxy) propionyl chloride, 3-(acryloylthioxy) propionoyl chloride, and 3-(N-acryloyl-N-methylamino) propionoyl chloride.

Representative anhydride group-substituted functional monomers include maleic anhydride, (meth)acrylic anhydride, itaconic anhydride, 3-(meth)acryloyloxyphthalic anhydride, and 2-(meth)acryloxycyclohexanedicarboxylic acid anhydride.

Preferred ethylenically unsaturated compounds having a reactive functional group ("functional acryl compounds") include hydroxyalkyl acrylates such as 2-hydroxyethyl (meth)acrylate and 2-(2-hydroxyethoxy)ethyl (meth)acrylate; aminoalkyl (meth)acrylates such as 3-aminopropyl (meth)acrylate and 4-aminostyrene; oxazolinyl compounds such as 2-ethenyl-1,3-oxazolin-5-one and 2-propenyl-4,4-dimethyl-1,3-oxazolin-5-one; carboxy-substituted compounds such as (meth)acrylic acid and 4-carboxybenzyl (meth)acrylate; isocyanato-substituted compounds such as isocyanatoethyl (meth)acrylate and 4-isocyanatocyclohexyl (meth)acrylate; epoxy-substituted compounds such as glycidyl (meth)acrylate; aziridinyl-substituted compounds such as N-acryloylaziridine and 1-(2-propenyl)-aziridine; and acryloyl halides such as (meth)acryloyl chloride.

It will also be understood that the compounds of Formula II may be provided with nucleophilic or electrophilic functional groups, in addition to simple ester or amides. With reference to the $X^2$ group of Formula II, which comprises an electrophilic or nucleophilic functional groups, $X^2$ may be selected from —OH, —Cl, —Br, —$NR^4H$, —$R^6$—NCO, —$R^6$—SH, —$R^6$—OH, —$R^6$—$NR^4H$, $R^6$—$Si(OR^4)_3$, $R^6$-halide, $R^6$-aziridine, $R^6$-epoxy, $R^6$—$N_3$, $R^6$-anhydride, $R^6$-succinate, $R^6$—$NR^4H$, and other electrophilic or nucleophilic functional groups.

wherein each $R^6$ is an alkylene group having 1 to 6 carbon atoms, a 5- or 6-membered cycloalkylene group having 5 to 10 carbon atoms, or a divalent aromatic group having 6 to 16 carbon atoms. $R^6$ may be substituted with one or more in-chain functional groups, including ether, amine, thioether, ester, amide, urea, and urethane functional groups, for example $R^6$—NH—CO—O—$R^{6'}$—NCO, where $R^{6'}$ is defined as $R^6$. $R^4$ is H or $C_1$-$C_4$ alkyl The present disclosure further provides a polymerizable composition comprising the addition-fragmentation agent of Formula I, and at least one polymerizable monomer, such as (meth)acryloyl monomers, including acrylate esters, amides, and acids to produce (meth)acrylate homo- and copolymers. Generally, the addition-fragmentation agent of Formula I is used in amounts of 0.1 to 10 parts by weight, preferably 0.1 to 5 parts by weight, based on 100 parts by weight of total monomer. The polymerizable composition may include a non-reactive organic solvent and is desirable non-aqueous, containing less than 0.1 wt. % water relative to the total weight of the polymerizable composition.

The (meth)acrylate ester monomer useful in preparing the (meth)acrylate polymer is a monomeric (meth)acrylic ester of a non-tertiary alcohol, which alcohol contains from 1 to 14 carbon atoms and preferably an average of from 4 to 12 carbon atoms.

Examples of monomers suitable for use as the (meth) acrylate ester monomer include the esters of either acrylic acid or methacrylic acid with non-tertiary alcohols such as ethanol, 1-propanol, 2-propanol, 1-butanol, 2-butanol, 1-pentanol, 2-pentanol, 3-pentanol, 2-methyl-1-butanol, 3-methyl-1-butanol, 1-hexanol, 2-hexanol, 2-methyl-1-pentanol, 3-methyl-1-pentanol, 2-ethyl-1-butanol, 3,5,5-trimethyl-1-hexanol, 3-heptanol, 1-octanol, 2-octanol, isooctyl-alcohol, 2-ethyl-1-hexanol, 1-decanol, 2-propylheptanol, 1-dodecanol, 1-tridecanol, 1-tetradecanol, citronellol, dihydrocitronellol, and the like. In some embodiments, the preferred (meth)acrylate ester monomer is the ester of (meth)acrylic acid with butyl alcohol or isooctyl alcohol, or a combination thereof, although combinations of two or more different (meth)acrylate ester monomer are suitable. In some embodiments, the preferred (meth)acrylate ester monomer is the ester of (meth)acrylic acid with an alcohol derived from a renewable source, such as 2-octanol, citronellol, dihydrocitronellol.

In some embodiments it is desirable for the (meth)acrylic acid ester monomer to include a high $T_g$ monomer, have a $T_g$ of at least 25° C., and preferably at least 50° C. Examples of suitable monomers useful in the present invention include, but are not limited to, t-butyl acrylate, methyl methacrylate, ethyl methacrylate, isopropyl methacrylate, n-butyl methacrylate, isobutyl methacrylate, s-butyl methacrylate, t-butyl methacrylate, stearyl methacrylate, phenyl methacrylate, cyclohexyl methacrylate, isobornyl acrylate, isobornyl methacrylate, benzyl methacrylate, 3,3,5 trimethylcyclohexyl acrylate, cyclohexyl acrylate, N-octyl acrylamide, and propyl methacrylate or combinations.

The (meth)acrylate ester monomer is present in an amount of up to 100 parts by weight, preferably 85 to 99.5 parts by weight based on 100 parts total monomer content used to prepare the polymer. Preferably (meth)acrylate ester monomer is present in an amount of 90 to 95 parts by weight based on 100 parts total monomer content. When high $T_g$ monomers are included, the copolymer may include up to 30 parts by weight, preferably up to 20 parts by weight of the (meth)acrylate ester monomer component.

The polymer may further comprise an acid functional monomer, where the acid functional group may be an acid per se, such as a carboxylic acid, or a portion may be salt thereof, such as an alkali metal carboxylate. Useful acid functional monomers include, but are not limited to, those selected from ethylenically unsaturated carboxylic acids, ethylenically unsaturated sulfonic acids, ethylenically unsaturated phosphonic acids, and mixtures thereof. Examples of such compounds include those selected from acrylic acid, methacrylic acid, itaconic acid, fumaric acid, crotonic acid, citraconic acid, maleic acid, oleic acid, β-carboxyethyl (meth)acrylate, 2-sulfoethyl methacrylate, styrene sulfonic acid, 2-acrylamido-2-methylpropanesulfonic acid, vinylphosphonic acid, and mixtures thereof.

Due to their availability, acid functional monomers of the acid functional copolymer are generally selected from ethylenically unsaturated carboxylic acids, i.e. (meth)acrylic acids. When even stronger acids are desired, acidic monomers include the ethylenically unsaturated sulfonic acids and ethylenically unsaturated phosphonic acids. The acid functional monomer is generally used in amounts of 0.5 to 15 parts by weight, preferably 1 to 15 parts by weight, most preferably 5 to 10 parts by weight, based on 100 parts by weight total monomer.

The polymer may further comprise a polar monomer. The polar monomers useful in preparing the copolymer are both somewhat oil soluble and water soluble, resulting in a distribution of the polar monomer between the aqueous and oil phases in an emulsion polymerization. As used herein the term "polar monomers" are exclusive of acid functional monomers.

Representative examples of suitable polar monomers include but are not limited to 2-hydroxyethyl (meth)acrylate; N-vinylpyrrolidone; N-vinylcaprolactam; acrylamide; mono- or di-N-alkyl substituted acrylamide; t-butyl acrylamide; dimethylaminoethyl acrylamide; N-octyl acrylamide; poly(alkoxyalkyl) (meth)acrylates including 2-(2-ethoxyethoxy)ethyl (meth)acrylate, 2-ethoxyethyl (meth)acrylate, 2-methoxyethoxyethyl (meth)acrylate, 2-methoxyethyl methacrylate, polyethylene glycol mono (meth)acrylates; alkyl vinyl ethers, including vinyl methyl ether; and mixtures thereof. Preferred polar monomers include those selected from the group consisting of 2-hydroxyethyl (meth)acrylate and N-vinylpyrrolidinone. The polar monomer may be present in amounts of 0 to 10 parts by weight, preferably 0.5 to 5 parts by weight, based on 100 parts by weight total monomer.

The polymer may further comprise a vinyl monomer. When used, vinyl monomers useful in the (meth)acrylate polymer include vinyl esters (e.g., vinyl acetate and vinyl propionate), styrene, substituted styrene (e.g., α-methyl styrene), vinyl halide, and mixtures thereof. As used herein vinyl monomers are exclusive of acid functional monomers, acrylate ester monomers and polar monomers. Such vinyl monomers are generally used at 0 to 5 parts by weight, preferably 1 to 5 parts by weight, based on 100 parts by weight total monomer.

In order to increase cohesive strength of composition, a multifunctional (meth)acrylate may be incorporated into the blend of polymerizable monomers. Multifunctional acrylates are particularly useful for emulsion or syrup polymerization. Examples of useful multifunctional (meth)acrylates include, but are not limited to, di(meth)acrylates, tri(meth) acrylates, and tetra(meth)acrylates, such as 1,6-hexanediol di(meth)acrylate, poly(ethylene glycol) di(meth)acrylates, polybutadiene di(meth)acrylate, polyurethane di(meth)acrylates, and propoxylated glycerin tri(meth)acrylate, and mixtures thereof. The amount and identity of multifunctional (meth)acrylate is tailored depending upon application of the adhesive composition. Typically, the multifunctional (meth) acrylate is present in amounts less than 5 parts based on total dry weight of adhesive composition. More specifically, the crosslinker may be present in amounts from 0.01 to 5 parts, preferably 0.05 to 1 parts, based on 100 parts total monomers of the adhesive composition.

In such embodiments, the copolymer may comprise:
i. up to 100 parts by weight, preferably 85 to 99.5 parts by weight of an (meth)acrylic acid ester;
ii. 0 to 15 parts by weight, preferably 0.5 to 15 parts by weight of an acid functional ethylenically unsaturated monomer;
iii. 0 to 15 parts by weight of a non-acid functional, ethylenically unsaturated polar monomer;
iv. 0 to 5 parts vinyl monomer;
v. 0 to 5 parts of a multifunctional (meth)acrylate;
vi. 0 to 5 parts of a polymerizable photoinitiator.
based on 100 parts by weight total monomer.

The composition may be polymerized with either a thermal initiator or photoinitiator. Any conventional free radical initiator may be used to generate the initial radical. Examples of suitable thermal initiators include peroxides such as benzoyl peroxide, dibenzoyl peroxide, dilauryl peroxide, cyclohexane peroxide, methyl ethyl ketone peroxide, hydroperoxides, e.g., tert-butyl hydroperoxide and cumene hydroperoxide, dicyclohexyl peroxydicarbonate, 2,2,-azo-bis(isobutyronitrile), and t-butyl perbenzoate. Examples of commercially available thermal initiators include initiators available from DuPont Specialty Chemical (Wilmington, Del.) under the VAZO trade designation including VAZO™ 67 (2,2'-azo-bis(2-methybutyronitrile)) VAZO™ 64 (2,2'-azo-bis(isobutyronitrile)) and VAZO™ 52 (2,2'-azo-bis(2,2-dimethyvaleronitrile)), and Lucidol™ 70 from Elf Atochem North America, Philadelphia, Pa.

Useful photoinitiators include benzoin ethers such as benzoin methyl ether and benzoin isopropyl ether; substituted acetophenones such as 2, 2-dimethoxyacetophenone, available as Irgacure™ 651 photoinitiator (Ciba Specialty Chemicals), 2,2 dimethoxy-2-phenyl-1-phenylethanone, available as Esacure™ KB-1 photoinitiator (Sartomer Co.; West Chester, Pa.), and dimethoxyhydroxyacetophenone; substituted α-ketols such as 2-methyl-2-hydroxy propiophenone; aromatic sulfonyl chlorides such as 2-naphthalenesulfonyl chloride; and photoactive oximes such as 1-phenyl-1,2-propanedione-2-(O-ethoxy-carbonyl)oxime. Particularly preferred among these are the substituted acetophenones.

The initiator is used in an amount effective to facilitate free radical addition to the addition-fragmentation crosslinking agent and the amount will vary depending upon, e.g., the type of initiator, and the molecular weight of the polymer and the degree of functionalization desired. The initiators can be used in amounts from about 0.001 part by weight to about 5 parts by weight based on 100 parts total monomer.

The curable composition may also include other additives. Examples of suitable additives include tackifiers (e.g., rosin esters, terpenes, phenols, and aliphatic, aromatic, or mixtures of aliphatic and aromatic synthetic hydrocarbon resins), surfactants, plasticizers (other than physical blowing agents), nucleating agents (e.g., talc, silica, or $TiO_2$), pigments, dyes, reinforcing agents, solid fillers, stabilizers (e.g., UV stabilizers), and combinations thereof. The additives may be added in amounts sufficient to obtain the desired properties for the cured composition being produced. The desired properties are largely dictated by the intended application of the resultant polymeric article.

In some embodiments the crosslinkable composition may include filler. In some embodiments the total amount of filler is at most 50 wt-%, preferably at most 30 wt-%, and more preferably at most 10 wt-% filler. Fillers may be selected from one or more of a wide variety of materials, as known in the art, and include organic and inorganic filler. Inorganic filler particles include silica, submicron silica, zirconia, submicron zirconia, and non-vitreous microparticles of the type described in U.S. Pat. No. 4,503,169 (Randklev).

Filler components include nanosized silica particles, nanosized metal oxide particles, and combinations thereof. Nanofillers are also described in U.S. Pat. No. 7,090,721 (Craig et al.), U.S. Pat. No. 7,090,722 (Budd et al.), U.S. Pat. No. 7,156,911 (Kangas et al.), and U.S. Pat. No. 7,649,029 (Kolb et al.).

The addition fragmentation agents are also useful in preparing dental compositions as described in Applicant's copending application titled "Dental Compositions Comprising Ethylenically Unsaturated Addition-Fragmentation Agent", U.S. Ser. No. 61/443,218 filed 15 Feb. 2011, incorporated by reference in its' entirety.

EXAMPLES

Examples 1-9. Addition-Fragmentation Monomer (AFM) Synthesis

General Procedures.

All reactions were performed in round-bottomed flasks or glass jars or vials using unpurified commercial reagents.

Materials.

Commercial reagents were used as received. Dichloromethane, ethyl acetate, and toluene were obtained from EMD Chemicals Inc. (Gibbstown, N.J., USA). Glycidyl methacrylate, 4-(dimethylamino)pyridine, methacryloyl chloride, triphenyl phosphine, 2,6-di-t-butyl-4-methylphenol, and dibutyltin dilaurate were obtained from Alfa Aesar (Ward Hill, Mass., USA). 2-Isocyantoethyl methacrylate, 1,2-epoxy-3-phenoxypropane, and 1,2-epoxydecane were obtained from TCI America (Portland, Oreg., USA). Acryloyl chloride, triethyl amine, and triphenyl antimony were obtained from Sigma Aldrich (St. Louis, Mo., USA). 4-hydroxybutyl acrylate glycidylether was obtained from Nippon Kasei Chemical (Tokyo, Japan). Glycidyl acrylate was obtained from Polysciences Inc. (Warringotn, Pa., USA). Methyl methacrylate oligomer mixture was obtained according to the procedure detailed in Example 1 of U.S. Pat. No. 4,547,323 (Carlson, G. M.).

Instrumentation.

Proton nuclear magnetic resonance (1H NMR) spectra and carbon nuclear magnetic resonance (13C NMR) spectra were recorded on a 400 MHz spectrometer.

Distillation of Methyl Methacrylate Oligomer Mixture[i]

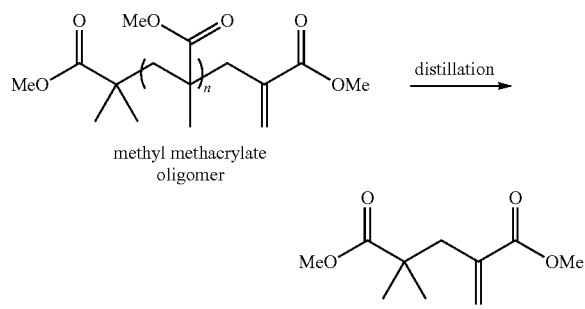

Distillation was performed as described in Moad, C. L.; Moad, G.; Rizzardo, E.; and Thang, S. H. *Macromolecules*, 1996, 29, 7717-7726, with details as follows: A 1 L round-bottomed flask equipped with a magnetic stir bar was charged with 500 g of methyl methacrylate oligomer mixture. The flask was fitted with a Vigreux column, a condenser, a distribution adapter, and four collection flasks. With stirring, the distillation apparatus was placed under reduced pressure (0.25 mm Hg). The oligomer mixture was stirred under reduced pressure at room temperature until gas evolution (removal of methyl methacrylate monomer) had largely subsided. The distillation pot was then heated to reflux in an oil bath to distill the oligomer mixture. The fractions isolated by this procedure are listed in Table 1

TABLE 1

Fractions from the Distillation of Methyl Methacrylate Oligomer Mixture

| Fraction | Pressure (mmHg) | Boiling point (° C.) | Mass (g) | Approximate Composition |
|---|---|---|---|---|
| A | 0.25 | 59 | 63.27 | Dimer |
| B | 0.09 | 47 | 115.97 | Dimer |
| C | 0.10 | 60-87 | 25.40 | dimer (~50-75%), oligomers (mainly trimer) |
| D | 0.10 | 87 | 15.20 | dimer (~5%), oligomers (mainly trimer) |
| E | 0.13 | 105 | 156.66 | oligomers (trimer and higher) |

Hydrolysis of Methyl Methacrylate Dimer

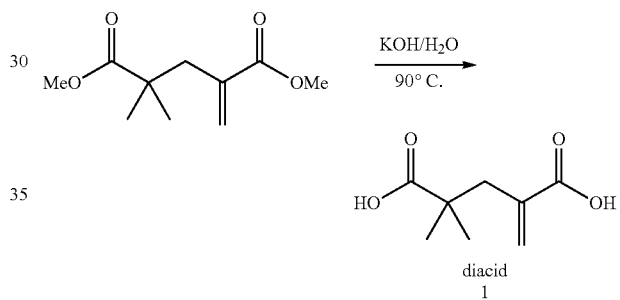

Hydrolysis of the dimer to Diacid 1 was performed as described in Hutson, L.; Krstina, J.; Moad, G.; Morrow, G. R.; Postma, A.; Rizzardo, E.; and Thang, S. H. *Macromolecules*, 2004, 37, 4441-4452, with details as follows:

A 1 L, round-bottomed flask equipped with a magnetic stir bar was charged with deionized water (240 mL) and potassium hydroxide (60.0 g, 1007 mmol). The mixture was stirred until homogeneous. Methyl methacrylate dimer (75.0 g, 374.6 mmol) was added. The reaction was equipped with a reflux condenser and was heated to 90° C. in an oil bath. After 17 hours, the reaction was removed from the oil bath and was allowed to cool to room temperature. The reaction solution was acidified to pH of approximately 1 using concentrated HCl. A white precipitate formed upon acidification. The heterogeneous mixture was vacuum filtered and quickly washed twice with 50-100 mL of deionized water. The white solid was dried by pulling air through the solid for approximately 4 hours. The white solid was then dissolved in approximately 1750 mL of dichloromethane. Only a very small amount (less than a gram) of solid remained insoluble. The solution was allowed to stand for 24 hours. The dichloromethane solution was then vacuum filtered to remove the undissolved white solid. The filtered dichloromethane solution was concentrated in vacuo to provide a white solid. The solid was further dried under high vacuum to provide diacid 1 (55.95 g, 325.0 mmol, 87%) as a white powder.

Example 1. Preparation of AFM-1

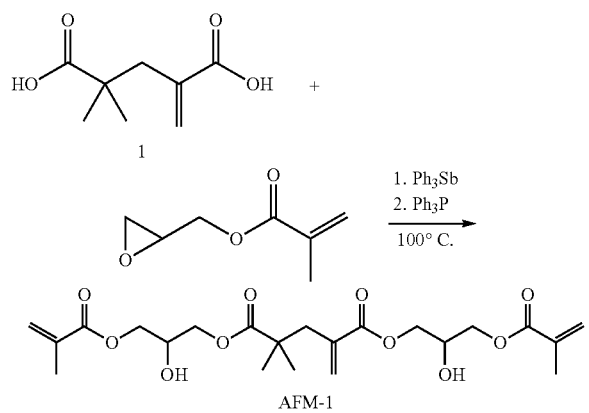

An approximately 250 mL amber bottle equipped with a magnetic stir bar was charged with glycidyl methacrylate (23.0 mL, 24.8 g, 174 mmol) and triphenyl antimony (0.369 g, 1.04 mmol). The reaction was covered with a plastic cap with two 16 gauge needles pierced through the cap to allow air into the reaction. With stirring, the mixture was heated to 100° C. in an oil bath. Diacid 1 (15.0 g, 87.1 mmol) was added to the reaction in small portions over a period of 1.5 hours. After 21 hours, triphenyl phosphine (0.091 g, 0.35 mmol) was added. The reaction was kept stirring at 100° C. After an additional 6.5 hours the reaction was sampled, and 1H NMR analysis was consistent with the desired product as a mixture of isomers and indicated consumption of glycidyl methacrylate. The reaction was cooled to room temperature to provide AFM-1 as a clear, very pale yellow viscous material.

Example 2. Preparation of AFM-2 Via Diol 2

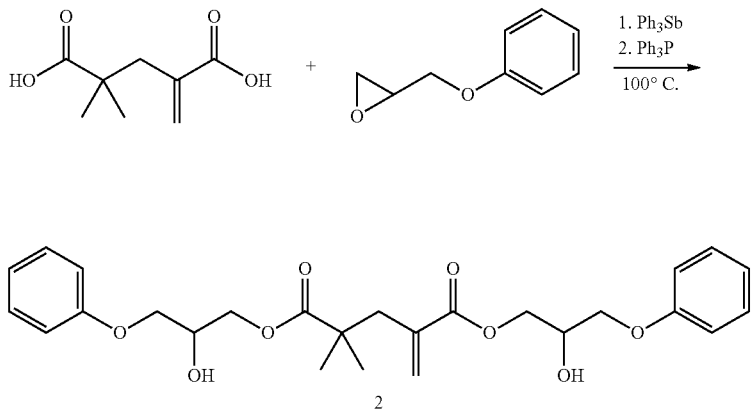

Preparation of Diol 2

An approximately 30 mL glass bottle equipped with a magnetic stir bar was charged with 1,2-epoxy-3-phenoxy-propane (3.93 mL, 4.36 g, 29.0 mmol) and triphenyl antimony (0.0593 g, 0.168 mmol). The reaction was sealed with a plastic cap. With stirring, the mixture was heated to 100° C. in an oil bath. Diacid 1 (2.50 g, 14.5 mmol) was added to the reaction in small portions over a period of 35 minutes. After 18 hours, triphenyl phosphine (0.0162 g, 0.0618 mmol) was added. The reaction was kept stirring at 100° C. After an additional 24 hours, the reaction was sampled and 1H NMR analysis was consistent with the desired product as a mixture of isomers. The reaction was cooled to room temperature to provide diol 2 as a clear, colorless glassy material.

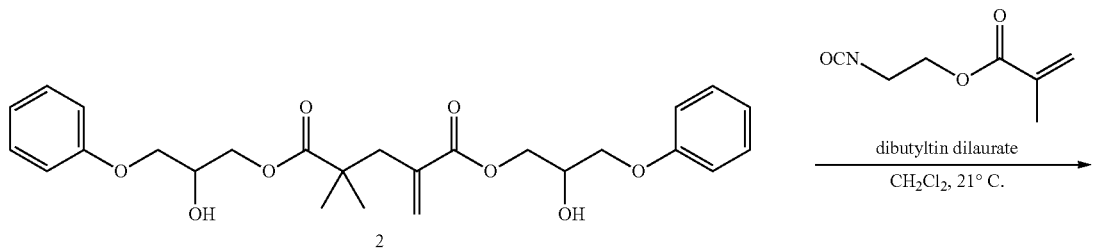

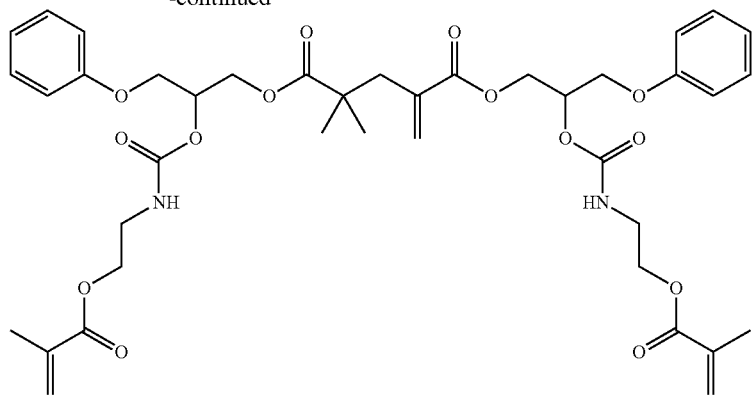

AFM-2

Preparation of AFM-2

A 100 mL round-bottomed flask equipped with a magnetic stir bar was charged with diol 2 (4.956 g, 10.49 mmol) and dichloromethane (20 mL). With stirring, 2-isocyanatoethyl methacrylate (2.20 mL, 2.416 g, 20.98 mmol) was added. Dibutyltin dilaurate (3 drops from a glass pipette) was added to the clear and homogeneous solution. The reaction was sealed with a plastic cap with a 16 gauge needle added to vent to air. After 72 hours, the reaction mixture was concentrated in vacuo to a clear viscous liquid. The liquid was transferred to a 25 mL amber bottle using a small amount of dichloromethane. Air was bubbled through the viscous material to remove solvent. 1H NMR analysis was consistent with the desired product as a mixture of isomers. AFM-2 (7.522 g, 9.63 mmol, 92%) was obtained as a very viscous, clear oil.

Example 3. Preparation of AFM-3

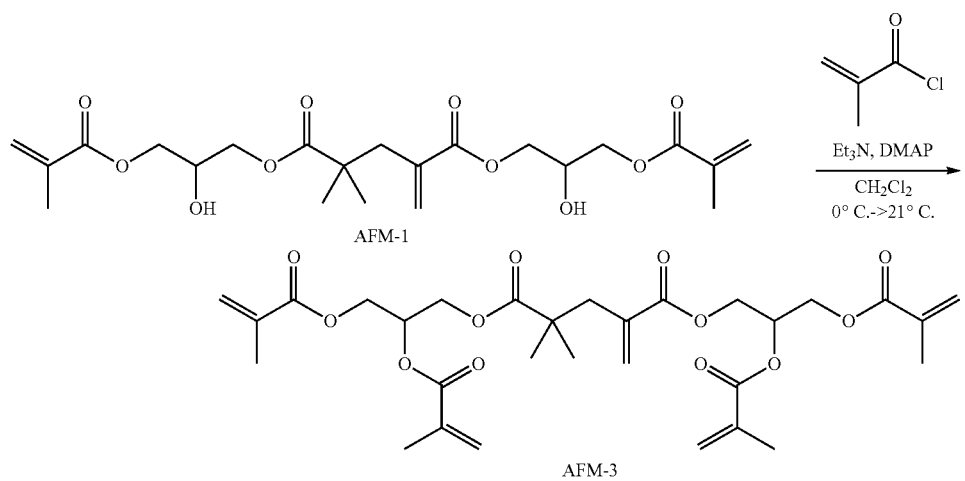

A two-neck, 500 mL round-bottomed flask equipped with a magnetic stir bar was charged with AFM-1 (20.00 g, 43.81 mmol) and dichloromethane (160 mL). The necks on the reaction flask were sealed with plastic caps and a 16 gauge needle was added to each cap to vent the reaction to air. The reaction was cooled to 0° C. with stirring. Triethylamine (30.5 mL, 22.1 g, 219 mmol) and 4-(dimethylamino)pyridine (1.609 g, 13.17 mmol) were added. Methacryloyl chloride (17.0 ml, 18.4 g, 176 mmol) was added to the reaction mixture dropwise over a period of 40 minutes. The pale yellow, heterogeneous reaction was allowed to slowly warm to room temperature. After 24 hours, the pale yellow reaction solution was concentrated in vacuo. Ethyl acetate (400 mL) was added to the residue and the mixture was transferred to a 1 L separatory funnel. The reaction flask was washed with aqueous hydrochloric acid (1N, 200 mL) and the aqueous hydrochloric acid solution was added to the separatory funnel. The solutions were mixed well and the aqueous layer was removed. The organic solution was further washed twice with 200 mL aqueous hydrochloric acid (1N), once with 200 mL of deionized water, three times with 200 mL of aqueous sodium hydroxide (1N), and once with 200 mL of a saturated aqueous solution of sodium chloride. The organic solution was dried over sodium sulfate for 30 minutes and then filtered. 2,6-di-t-butyl-4-methylphenol (0.011 g) was added, and the solution was concentrated in vacuo (bath temperature less than 20° C.) to a viscous solution. The concentrated solution was transferred to an amber bottle using a small amount of dichloromethane to ensure quantitative transfer. Air was bubbled through the viscous material to remove solvent. 1H NMR analysis was consistent with the desired product as a mixture of isomers. AFM-3 (23.44 g, 39.55 mmol, 90%) was obtained as a very viscous, very pale yellow oil.

Example 4. Preparation of AFM-4

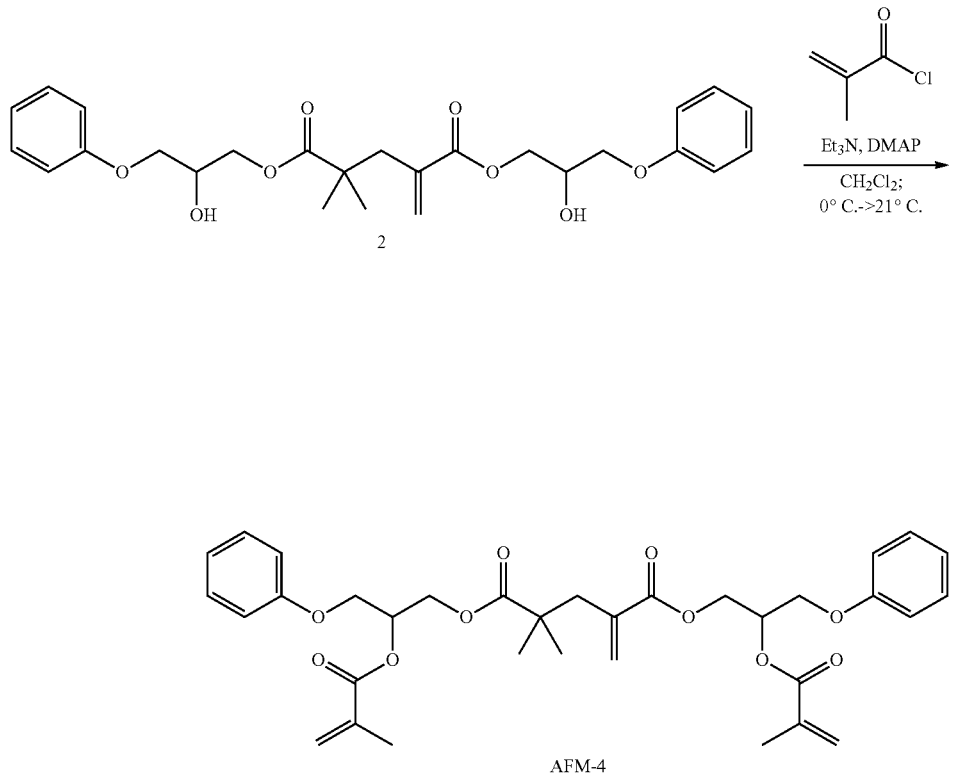

A three-neck, 250 mL round-bottomed flask was equipped with a magnetic stir bar. Diol 2 (6.86 g, 14.52 mmol) was dissolved in dichloromethane (25 mL) and added to the reaction flask. Five additional 5 mL portions of dichloromethane were used to ensure quantitative transfer of diol 2 and these rinses were added to the reaction flask. The reaction flask was equipped with a pressure-equalizing addition funnel capped with a plastic cap. The other two necks on the reaction flask were also sealed with plastic caps, and a 16 gauge needle was added to each to vent the reaction to air. The reaction was cooled to 0° C. with stirring. Triethylamine (10.0 mL, 7.26 g, 71.8 mmol) and 4-(dimethylamino)pyridine (0.532 g, 4.36 mmol) were added. A 37.3 wt. % solution of methacryloyl chloride in toluene (16.28 g solution, 6.07 g methacryloyl chloride, 58.1 mmol) was added to the addition funnel. The toluene solution of methacryloyl chloride was added to the reaction mixture dropwise over a period of 30 minutes. The reaction became pale yellow. After 18 hours, the pale yellow reaction solution was transferred to a 500 mL separatory funnel using dichloromethane (200 mL). The organic solution was washed twice with 150 mL of aqueous hydrochloric acid (1N), once with 150 mL of deionized water, twice with 150 mL of aqueous sodium hydroxide (1N), and once with 200 mL of a saturated aqueous solution of sodium chloride. The organic solution was dried over sodium sulfate for 30 minutes, and was then filtered and concentrated in vacuo (bath temperature less than 20° C.) to a viscous solution. The concentrated solution was transferred to an amber bottle using a small amount of dichloromethane to ensure quantitative transfer. Air was bubbled through the viscous material to remove solvent. 1H NMR analysis was consistent with the desired product as a mixture of isomers. AFM-4 (8.463 g, 13.9 mmol, 96%) was obtained as a very viscous, pale yellow oil.

Example 5. Preparation of AFM-5

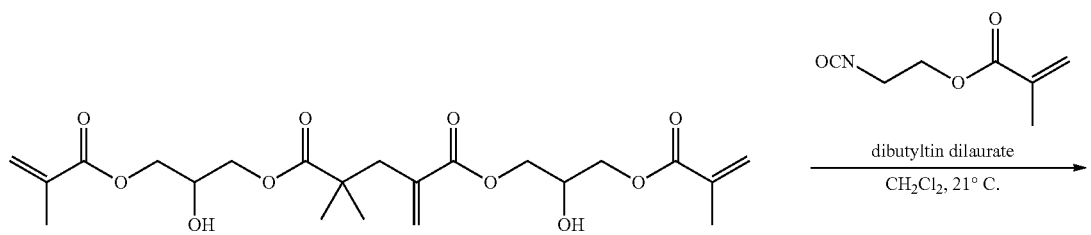

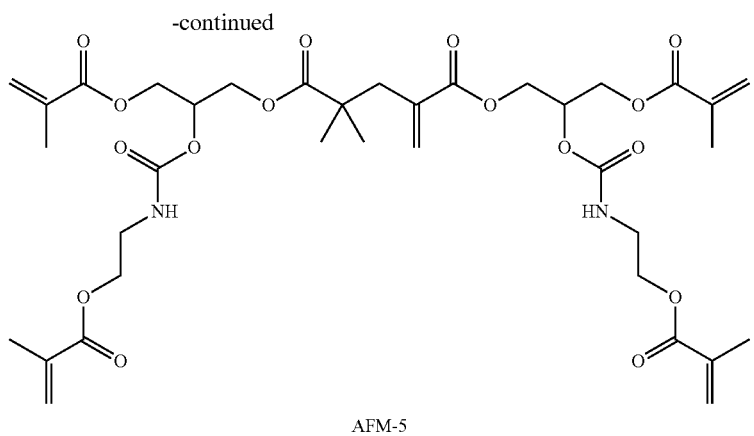

AFM-5

A 500 mL round-bottomed flask equipped with a magnetic stir bar was charged with AFM-1 (31.40 g, 68.79 mmol) and dichloromethane (210 mL). With stirring, 2-isocyanatoethyl methacrylate (19.4 mL, 21.3 g, 137 mmol) was added. Dibutyltin dilaurate (3 drops from a glass pipette) was added to the clear and homogeneous solution. The reaction was sealed with a plastic cap and two 16 gauge needles were added to vent to air. After 48 hours, the reaction mixture was concentrated in vacuo to a clear viscous liquid. The liquid was transferred to an approximately 100 mL amber bottle using a small amount of dichloromethane. Air was bubbled through the viscous material to remove solvent. 1H NMR analysis was consistent with the desired product as a mixture of isomers. AFM-5 (37.60 g, 49.04 mmol, 71%) was obtained as a very viscous, clear oil.

Example 6. Preparation of AFM-6

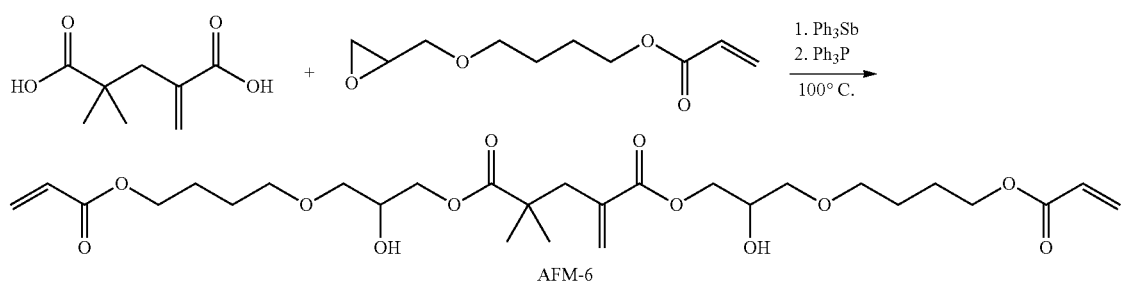

An approximately 25 mL amber bottle equipped with a magnetic stir bar was charged with 4-hydroxybutyl acrylate glycidylether (4.6516 g, 23.23 mmol) and triphenyl antimony (0.0492 g, 0.139 mmol). The reaction vessel was covered with a plastic cap and two 16 gauge needles were inserted through the cap to allow air into the reaction. With stirring, the mixture was heated to 100° C. in an oil bath. Diacid 1 (2.000 g, 11.62 mmol) was added to the reaction in small portions over a period of 15 minutes. After 24 hours, triphenyl phosphine (0.0122 g, 0.0465 mmol) was added. The reaction was kept stirring at 100° C. After an additional 21 hours the reaction was sampled, and 1H NMR analysis was consistent with the desired product as a mixture of isomers and indicated consumption of 4-hydroxybutyl acrylate glycidylether. The reaction was cooled to room temperature to provide AFM-6 as a clear, very pale yellow viscous material.

Example 7. Preparation of AFM-7

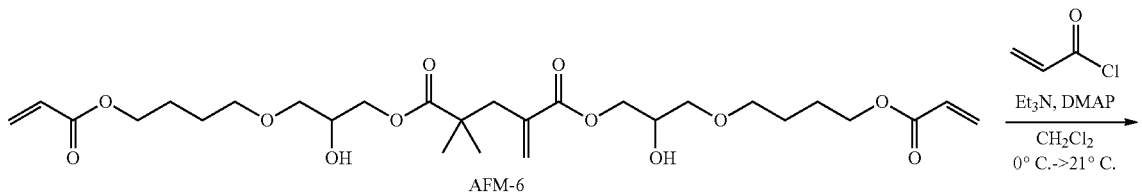

-continued

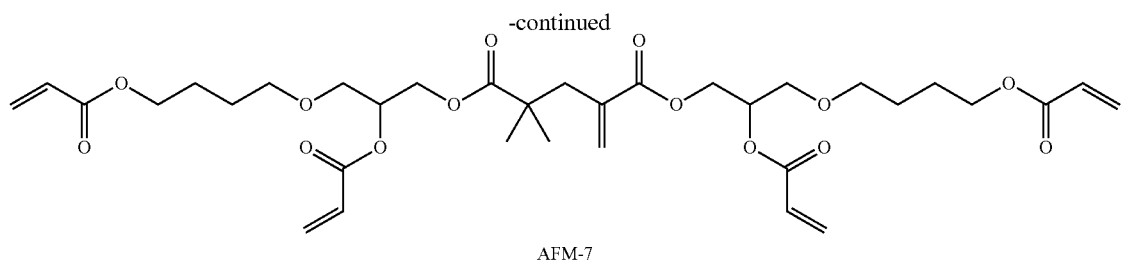

AFM-7

A three-neck, 100 mL round-bottomed flask equipped with a magnetic stir bar was charged with AFM-6 (5.00 g, 8.731 mmol) and dichloromethane (40 mL). The necks on the reaction flask were sealed with plastic caps and a 16 gauge needle was added to two of the caps to vent the reaction to air. The reaction was cooled to 0° C. with stirring. Triethylamine (6.1 mL, 4.43 g, 43.8 mmol) and 4-(dimethylamino)pyridine (0.320 g, 2.62 mmol) were added. Acryloyl chloride (2.84 ml, 3.16 g, 34.9 mmol) was added to the reaction mixture dropwise over a period of 30 minutes. The pale yellow, heterogeneous reaction was allowed to slowly warm to room temperature. After 48 hours, the pale yellow reaction solution was concentrated in vacuo. Ethyl acetate (100 mL) was added to the residue and the mixture was transferred to a 500 mL separatory funnel. The reaction flask was washed with aqueous hydrochloric acid (100 mL) and the aqueous hydrochloric acid solution was added to the separatory funnel. The solutions were mixed well and the aqueous layer was removed. The organic solution was further washed twice with 100 mL of aqueous hydrochloric acid (1N), once with 100 mL of deionized water, three times with 100 mL of aqueous sodium hydroxide (1N), and once with 100 mL of a saturated aqueous solution of sodium chloride. The organic solution was dried over sodium sulfate for 30 minutes and then filtered. 2,6-di-t-butyl-4-methylphenol (0.003 g) was added, and the solution was concentrated in vacuo (bath temperature less than 20° C.) to a viscous solution. The concentrated solution was transferred to an amber bottle using a small amount of dichloromethane to ensure quantitative transfer. Air was bubbled through the viscous material to remove solvent. 1H NMR analysis was consistent with the desired product as a mixture of isomers. AFM-7 (5.03 g, 7.39 mmol, 85%) was obtained as a very viscous, very pale yellow oil.

Example 8. Preparation of AFM-8 Via Diol 3

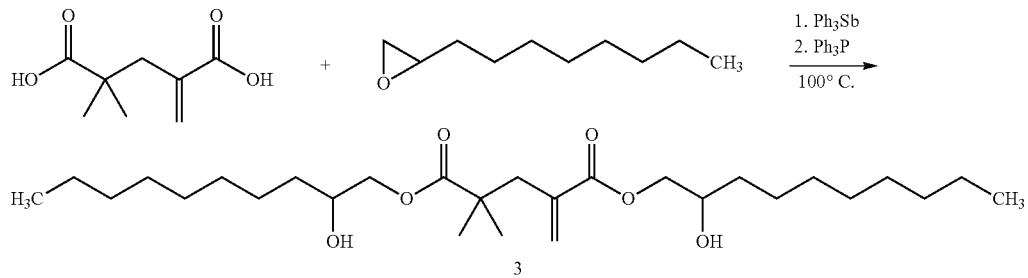

Preparation of Diol 3

A glass vial equipped with a magnetic stir bar was charged with 1,2-epoxydecane (4.53 g, 29.0 mmol) and triphenyl antimony (0.102 g, 0.29 mmol). The reaction vial was sealed with a plastic cap. With stirring, the mixture was heated to 100° C. in an oil bath. Diacid 1 (2.50 g, 14.5 mmol) was added to the reaction in small portions over a period of 1 hour. After 1 day, triphenyl phosphine (0.0259 g, 0.098 mmol) was added. The reaction was kept stirring at 100° C. for an additional 18 hours. It was then sampled and 1H NMR analysis was consistent with the desired product as a mixture of isomers. The reaction was cooled to room temperature to provide diol 3 as a viscous, light yellow oil.

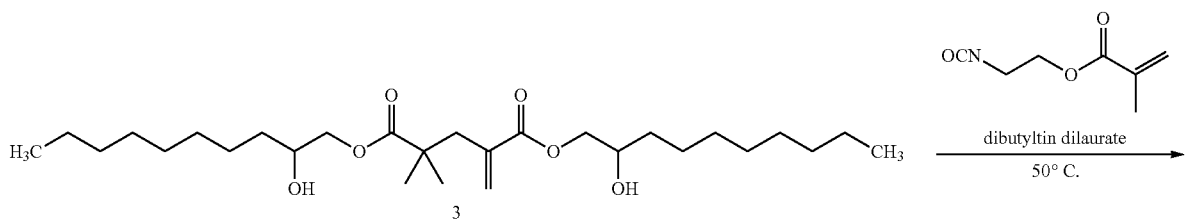

-continued

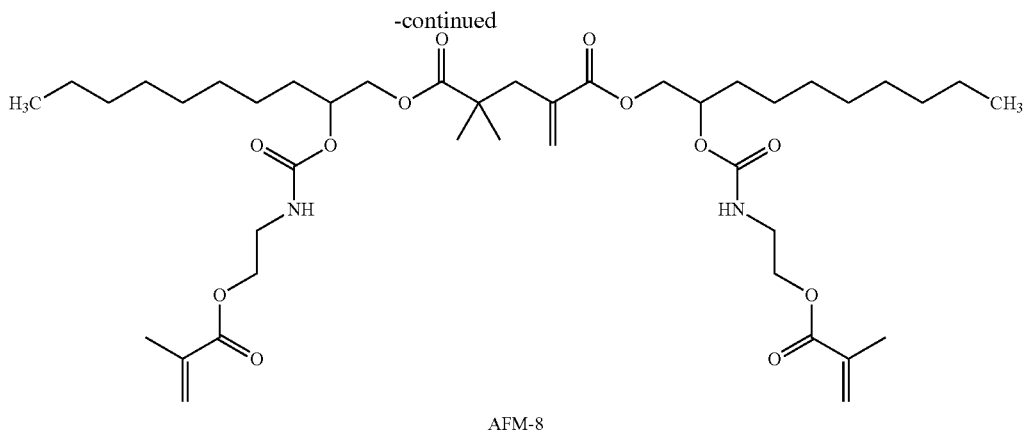

AFM-8

Preparation of AFM-8

A glass vial equipped with a magnetic stir bar was charged with diol 3 (1.00 g, 2.063 mmol) and 2-isocyanatoethyl methacrylate (0.644 g, 4.15 mmol). Dibutyltin dilaurate (6 drops from a glass pipette) was added to the homogeneous solution. The reaction was kept open to air and, with stirring, the mixture was heated to 50° C. in an oil bath. After 18 hours, the reaction was sampled and 1H NMR analysis was consistent with the desired product as a mixture of isomers. The reaction was cooled to room temperature, and AFM-8 was obtained as a very viscous, light yellow oil.

Example 9. Preparation of AFM-9

An approximately 250 mL clear bottle was charged with glycidyl acrylate (0.169 g, 1.32 mmol), diacid 1 (0.1142 g, 0.66 mmol), and triphenyl antimony (0.0027 g, 0.0076 mmol). The reaction was covered with a plastic cap and heated to 100° C. After 16 hours, triphenyl phosphine (0.0007 g, 0.0027 mmol) was added. The reaction was kept at 100

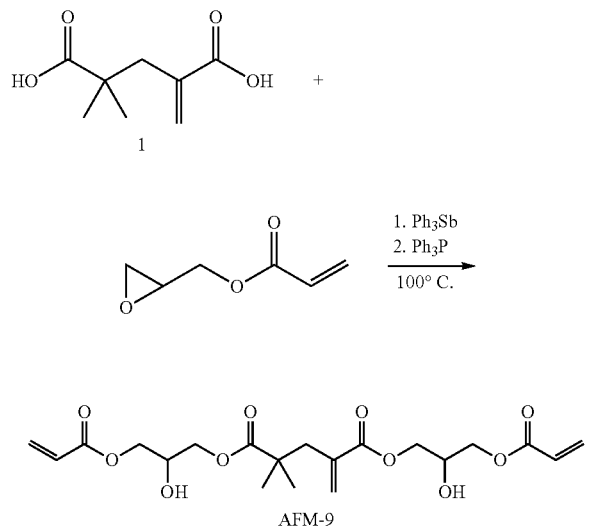

AFM-9

° C. After an additional 23 hours the reaction was sampled, and $^1$H NMR analysis was consistent with the desired product as a mixture of isomers and indicated consumption of glycidyl acrylate. The reaction was cooled to room temperature to provide AFM-9 as a clear, very pale yellow viscous material.

Examples 10-14

For each of Examples 10-14, 450 g of isooctyl acrylate (IOA, 90 parts), 50 g of acrylic acid (AA, 10 parts), and 0.2 g (0.04 pph) of 2,2-dimethoxy-2-phenylacetophenone photoinitiator (IRGACURE 651; BASF Corporation; Florham Park N.J., USA) were added to a glass reaction vessel. The vessel was capped, and purged with nitrogen for 20 minutes. The reaction mixture was then exposed to low intensity UV radiation from a SYLVANIA F40/350 BL 40 watt fluorescent "black light" (Osram Sylvania; Danvers Mass., USA) until it reached a coatable viscosity (about 5000 cps). Then, with stirring, 0.8 g (0.16 pph) of additional IRGACURE 651 photoinitiator was added along with an amount of AFM-6 which varied for each of Examples 10-14. The amounts of added AFM-6 are shown in Table 2, in weight % of AFM-6 in the mixture.

For each of Examples 10-14, an adhesive-coated sheet was prepared by knife coating the composition thus prepared to a thickness of about 2 mil (about 50 micrometers) onto the primed side of a clear polyester film, HOSTAPHAN 3SAB (Mitsubishi Polyester Film, Inc.; Greer, S.C., USA). The coating was then covered with a clear silicone coated film, SILPHAN S 36 M74A (Siliconature USA, LLC; Chicago, Ill., USA). This sandwich construction was then irradiated with UVA light (650 mJ/cm$^2$) to cure the coating to an adhesive.

The adhesive coated sheets were cut into tape strips, conditioned at 23° C./50% Relative Humidity for 24 hours, and then tested for 180 degree peel adhesion on glass. Peel adhesion testing was carried out according to ASTM D 3330/D 3330M-04, except that glass, rather than stainless steel, was used as the substrate, and the tape strips tested were ½" (12.7 mm) in width, rather than 1" (25.4 mm). Each test sample was prepared by removing the silicone liner from a 12.7 mm wide conditioned tape and adhering the adhesive coated side of the coated polyester film to a glass plate, rolling over the tape four times with a 2-kilogram roller. The tape was then peeled from the glass at 180 degrees peel angle, using a tensile force tester at a platen speed of 12 inches/min (305 mm/min). Three identically-prepared specimens were tested for each Example. The averaged values for the three replicates are reported in Table 2, in both Newtons per decimeter (N/dm) and ounces per inch (oz/in).

TABLE 2

180 degree Peel Values for Adhesive Tapes Made Using AFM-6

| Ex. No. | AFM-6 Amount weight % in mixture | 180° Peel Value N/dm (oz/in) |
|---|---|---|
| 10 | 0 | 97 (89) |
| 11 | 0.5 | 68 (62) |
| 12 | 1.2 | 61 (56) |
| 13 | 2 | 51 (47) |
| 14 | 3.4 | 39 (36) |

The use of the addition-fragmentation agents in dental composition, the stress-strain behavior, and other physical properties is further illustrated with the following Examples from Applicant's application U.S. Ser. No. 61/443,218, filed 15 Feb. 2011, and incorporated herein by reference.

The use of the addition-fragmentation agents in dental composition, the stress-strain behavior, and other physical properties is further illustrated with the following Examples from Applicant's application U.S. Ser. No. 61/443,218, filed 15 Feb. 2011, and incorporated herein by reference.

Materials

BisGMA (2,2-bis[4-(2-hydroxy-3-methacryloyloxy-propoxy)phenyl]propane (Sigma Aldrich, St. Louis, Mo.)

TEGDMA (triethyleneglycol dimethacrylate, Sartomer Co., Inc., Exton, Pa.)

UDMA (Diurethane dimethacrylate, CAS No. 41137-60-4, commercially available as Rohamere 6661-0, Rohm Tech, Inc., Malden, Mass.)

BisEMA6 (ethoxylated bisphenol A methacrylate as further described in U.S. Pat. No. 6,030,606, available from Sartomer as "CD541")

CPQ (camphorquinone, Sigma Aldrich, St. Louis, Mo.)

EDMAB (ethyl 4-(N,N-dimethylamino) benzoate, Sigma Aldrich)

DPIHFP (diphenyl iodonium hexafluorophosphate, Alpha Aesar, Ward Hill, Mass.)

BHT (butylated hydroxytoluene, Sigma Aldrich)

BZT (refers to 2-(2-hydroxy-5-methacryloxyethylphenyl)-2H-benzotriazole, Ciba, Inc., Tarrytown, N.Y.)

TCD alcohol refers to tricyclodecane dimethanol (tricyclo [5.2.1.02,6]decane dimethanol, CAS: 26160-83-8) available from Celanese HEMA (2-hydroxyethyl methacrylate, Sigma-Aldrich)

Tris-(2-hydroxyethyl)isocyanurate (TCI America, Portland, Oreg.)

DCC (dicyclohexyl carbodimide, TCI)

YbF$_3$ (ytterbium fluoride, Treibacher, Germany)

Zr/Si filler (surface treated, one hundred parts zirconia silica filler of average particle size 0.6-0.9 micrometers was mixed with deionized water at a solution temperature of between 20-30° C., and the pH is adjusted to 3-3.3 with trifluoroacetic acid (0.278 parts). A-174 silane (SILQUEST A-174, gamma.-methacryloxypropyltrimethoxysilane, Crompton Corporation, Naugatuck, Conn.) was added to the slurry in an amount 7 parts and the blend is mixed over 2 hours. At the end of 2 hours, the pH is neutralized with calcium hydroxide. The filler is dried, crushed and screened through a 74 or 100 micron screen.)

Zr/Si Nano-Cluster Filler (silane-treated zirconia/silica nanocluster filler prepared essentially as described in U.S. Pat. No. 6,730,156 (Preparatory Example A and Example B)

Isocyanurate Trimer—Synthesis of Tri-HydroxyEthyl Iso Cyanurate Tris HEMA Phthalate Phthalic acid anhydride (57.0 g, 0.385 mol, CAS #85-33-9, Alfa Aesar, lot G30T004), 4-(dimethylamino)pyridine (DMAP, 4.9 g, 0.04 mol, CAS #1122-58-3, Alfa Aesar, lot L125009), 2-hydoxyethylmethacrylate (HEMA, 50.9 g, 0.391 mol, and butylated hydroxytoluene (BHT, 0.140 g) were charged into a 2-liter 3-neck reaction flask equipped with a mechanical stirrer, a thermocouple connected to a temperature controller, a dry air stream running through a T-shape connection into the reactor then to an oil bubbler, and a heating mantle. With continuous stirring, the flask contents were heated to 95° C., by which all components dissolved and a clear liquid was obtained. Heating at 95° C. and stirring were continued for 5 hours. The heat was turned off and the flask contents were allowed to cool to room temperature while still being stirred under dry air. Acetone (250 ml) was added followed by tris-(2-hydroxyethyl)isocyanurate (33.58 g, 0.158 mol, from TCI). The heating mantle was replaced with an ice bath, where the mixture was cooled to 0-5° C. A solution made from dicyclohexyl carbodiimide (DCC, 81 g, 0.393 mol) in 120 ml acetone was placed into a 500 ml dropping funnel which was placed in-between the reaction flask and the dry air in-let. The DCC solution was added slowly to the continuously stirred reaction mixture in a rate where the reaction mixture temperature would not exceed 10° C. After complete addition of the DCC solution, the reaction was stirred in the ice bath for 2 hours in at room temperature overnight. On day 2, the solid formed was removed by vacuum filtration and the residue was concentrated in a rotary evaporator at 40-45° C. bath. The residue was dissolved in 300 ml solution of ethylacetate: hexanes, 2:1 by volume. The obtained solution was extracted with 200 ml of 1.0 N. HCl, 200 ml of 10% aqueous, 200 ml H$_2$O, and 200 ml brine. The organic layer was concentrated in a rotary evaporator with 40° C. bath. Further drying was done under a vacuum pump at 50° C. for 3 hours with air bleeding into the product during the whole time to give an almost colorless hazy viscous liquid.

Refractive index was measured and found to be 1.5386. By use of NMR the liquid was determined to be the product shown is the following reaction scheme. The calculated molecular weight of the depicted end product was determined to be 1041 g/mole.

The calculated molecular weight of the linking group was determined to be 220 g/mole.

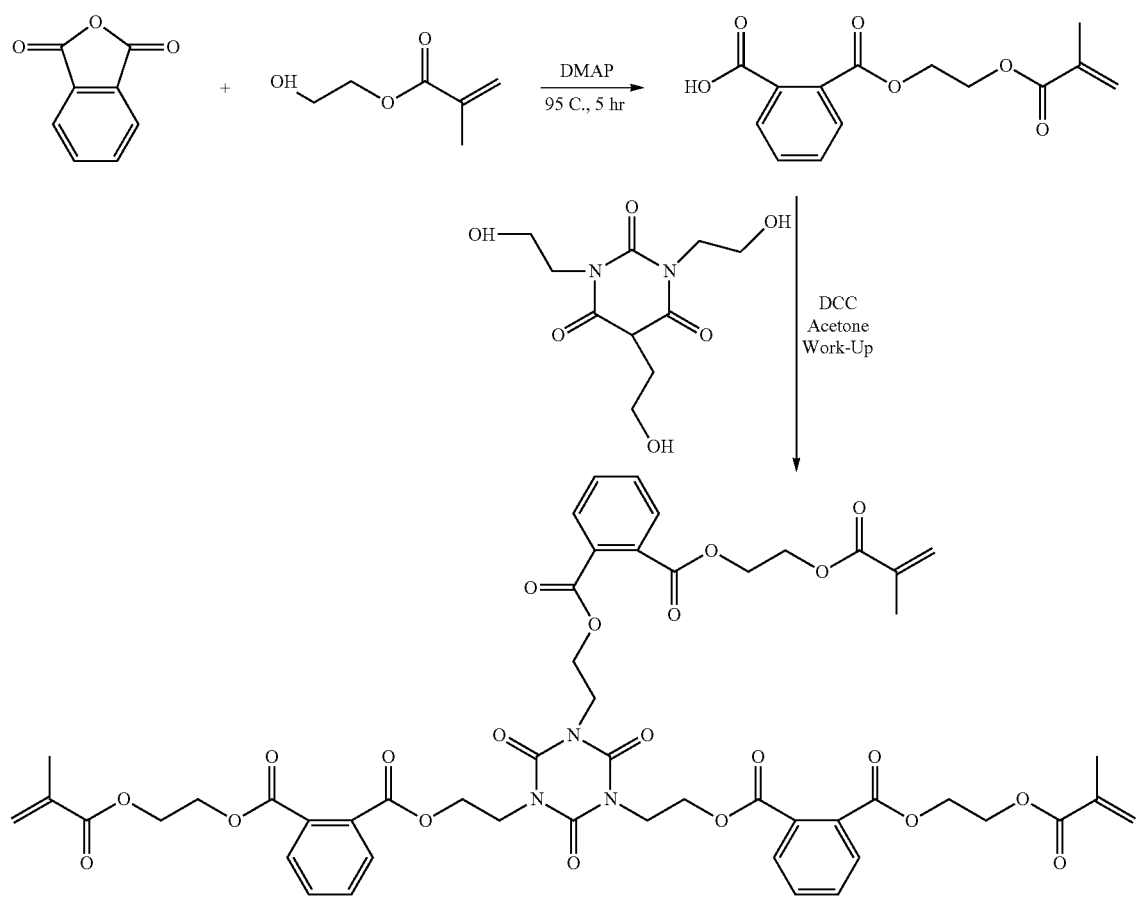

Synthesis of TGP-IEM
General Procedure 1: Reaction of a Diol-Precursor with Epoxiy Components Using TEAA as Catalyst E.g. TCD alcohol and GMA as the corresponding epoxy functional reagent/s are mixed while stirring with e.g. cyclohexane. 1.5 wt.-% of TEA and 1.5 wt.-% of GAA (with respect to the mass of the sum of all reactants, to form in situ TEAA), 1000 ppm of HQ, 200 ppm of BHT, and 200 ppm of HQME are added while stirring. Then the mixture is heated while stirring a temperature of about 70° C. until completion of the addition reaction (measured via 1H-NMR: no signals of residual epoxy groups were detected). Optionally, 3 to 5 wt.-% of MSA is slowly added while stirring and stirring is continued for about 60 min at about 70° C. Then the mixture is allowed to cool to room temperature while stirring. The upper cyclohexane phase is separated from the oily viscous lower phase if existent. The separated cyclohexane phase is washed once with water, then extracted twice with 2N NaOH solution, then once washed with water, then dried over anhydrous $Na_2SO_4$. After filtration, the filtrate is again filtered through basic alumina. 100 ppm of BHT and 100 ppm of HQME are added to the filtrate. Then the solvent is stripped off in vacuum while air is bubbling through the crude sample.

According to General Procedure 1 100 g of TCD alcohol, 155 g of GP, and 3.00 g of MSA were reacted. 253 g of TGP (509 mmol, 99%) were isolated as yellow oil. According to General Procedure 4 100 g of TGP and 59.4 g of IEM were reacted. 158 g of TGP-IEM (196 mmol, 99%) were isolated as yellow oil: $\eta$=1400 Pa*s, $n_D^{20}$=1.531.

Synthesis of TTEO-IEM
General Procedure 2: Reaction of a Diol-Precursor Like with Epoxy Components Containing Mixtures (e.g. EO in THF) Using $BF_3$*THF as Catalyst E.g. TCD alcohol is diluted in anhydrous THF, then $BF_3$*THF is added while stirring. Gaseous EO is added while stirring so that the temperature of the reaction mixture does not exceed about 30-40° C. After completion of the EO addition stirring is continued at room temperature for about 30 min. 13 wt.-% of water (with respect to the sum of the amounts of the reactive educts) are added, after about 30 min while stirring 13 wt.-% of basic alumina is added, too. After additional about 60 min of stirring 13 wt.-% of a solution of sodium methanolate in methanol (30% in methanol) is added. Then the suspension is stirred at room temperature for about 12 h. After filtration the solvent is stripped off in vacuum.

According to General Procedure 2 300 g of TCD alcohol, 64.6 g of EO, 600 g of THF, and 37.9 g of $BF_3$*THF were reacted. 429 g of TTEO were isolated as colorless oil. According to General Procedure 4 55.3 g of TTEO and 54.7 g of IEM were reacted. 100 g of TTEO-IEM (95%) were isolated as colorless oil: $\eta$=45 Pa*s, $n_D^{20}$=1.503.

Synthesis of TTEO-MA:
General Procedure 3: Reaction of a Diol-Precuror Like e.g. TCD Alcohol with Epoxy Containing Mixtures (e.g. EO in THF) Using $BF_3$*THF as Catalyst E.g. TCD alcohol is diluted in anhydrous THF, then $BF_3$*THF is added while stirring. Gaseous EO is added while stirring so that the temperature of the reaction mixture does not exceed about 30-40° C. After completion of the EO addition stirring is continued at room temperature for about 30 min. 13 wt.-% of water (with respect to the sum of the amounts of the reactive educts) are added, after about 30 min while stirring 13 wt.-% of basic alumina is added, too. After additional about 60 min of stirring 13 wt.-% of a solution of sodium methanolate in methanol (30% in methanol) is added. Then the suspension is stirred at room temperature for about 12 h. After filtration the solvent is stripped off in vacuum.

According to General Procedure 3 300 g of TCD alcohol, 64.6 g of EO, 600 g of THF, and 37.9 g of $BF_3$*THF were reacted. 429 g of TTEO were isolated as colorless oil. According to General Procedure 4 213 g of TTEO, 161 g of MA, 44.8 mg of BHT, 121 mg of HQME, 89.6 mg of methylene blue, and 12.8 g of MSA were reacted using hexane as solvent. 237 g of TTEO-MA (67%) were isolated as colorless liquid: $\eta=0.1$ Pa*s, $n_D^{20}=1.499$.

Test Methods

Stress Test Method

To measure stress development during the curing process, a slot was machined into a rectangular 15×8×8 mm aluminum block. The slot was 8 mm long, 2.5 mm deep, and 2 mm across, and was located 2 mm from an edge, thus forming a 2 mm wide aluminum cusp adjacent to a 2 mm wide cavity containing dental compositions being tested. A linear variable displacement transducer (Model GT 1000, used with an E309 analog amplifier, both from RDP Electronics, United Kingdom) was positioned as shown to measure the displacement of the cusp tip as the dental composition photocured at room temperature. Prior to testing, the slot in the aluminum block was sandblasted using Rocatec Plus Special Surface Coating Blasting Material (3M ESPE), treated with RelyX Ceramic Primer (3M ESPE), and finally treated with a dental adhesive, Adper Easy Bond (3M ESPE).

The slot was fully packed with the mixtures shown in the tables, which equalled approximately 100 mg of material. The material was irradiated for 1 minute with a dental curing lamp (Elipar S-10, 3M ESPE) positioned almost in contact (<1 mm) with the material in the slot, then the displacement of the cusp in microns was recorded 9 minutes after the lamp was extinguished.

Watts Shrinkage Test Method

The Watts Shrinkage (Watts) Test Method measures shrinkage of a test sample in terms of volumetric change after curing. The sample preparation (90-mg uncured composite test sample) and test procedure were carried out as described in the following reference: Determination of Polymerization Shrinkage Kinetics in Visible-Light-Cured Materials: Methods Development, Dental Materials, October 1991, pages 281-286. The results are reported as negative % shrinkage.

Diametral Tensile Strength (DTS) Test Method

Diametral tensile strength of a test sample was measured according to the following procedure. An uncured composite sample was injected into a 4-mm (inside diameter) glass tube; the tube was capped with silicone rubber plugs. The tube was compressed axially at approximately 2.88 kg/cm² pressure for 5 minutes. The sample was then light cured for 80 seconds by exposure to a XL 1500 dental curing light (3M Company, St. Paul, Minn.), followed by irradiation for 90 seconds in a Kulzer UniXS curing box (Heraeus Kulzer GmbH, Germany). The sample was cut with a diamond saw to form disks about 2 mm thick, which were stored in distilled water at 37° C. for about 24 hours prior to testing. Measurements were carried out on an Instron tester (Instron 4505, Instron Corp., Canton, Mass.) with a 10 kilonewton (kN) load cell at a crosshead speed of 1 mm/minute according to ISO Specification 7489 (or American Dental Association (ADA) Specification No. 27). Samples were prepared and measured with results reported in MPa as the average of multiple measurements.

Barcol Hardness Test Method

Barcol Hardness of a test sample was determined according to the following procedure. An uncured composite sample was cured in a 2.5-mm or 4-mm thick TEFLON mold sandwiched between a sheet of polyester (PET) film and a glass slide for 20 seconds and cured with an ELIPAR Freelight 2 dental curing light (3M Company). After irradiation, the PET film was removed and the hardness of the sample at both the top and the bottom of the mold was measured using a Barber-Coleman Impressor (a hand-held portable hardness tester; Model GYZJ 934-1; Barber-Coleman Company, Industrial Instruments Division, Lovas Park, Ind.) equipped with an indenter. Top and bottom Barcol Hardness values were measured at 5 minutes after light exposure.

Depth of Cure Test Method

The depth of cure was determined by filling a 10 millimeter stainless steel mold cavity with the composite, covering the top and bottom of the mold with sheets of polyester film, pressing the sheets to provide a leveled composition surface, placing the filled mold on a white background surface, irradiating the dental composition for 20 seconds using a dental curing light (3M Dental Products Curing Light 2500 or 3M ESPE Elipar FreeLight2, 3M ESPE Dental Products), separating the polyester films from each side of the mold, gently removing (by scraping) materials from the bottom of the sample (i.e., the side that was not irradiated with the dental curing light), and measuring the thickness of the remaining material in the mold. The reported depths are the actual cured thickness in millimeters divided by 2.

Flexural Strength and Flexural Modulus Test Method

A paste sample was extruded into a 2 mm×2 mm×25 mm quartz glass mold forming a test bar. The material was then cured through the mold using 2 standard dental cure lights (3M ESPE XL2500 or 3M ESPE XL3000). The samples were cured by placing one light in the center of the sample bar, curing for 20 sec, then simultaneously curing the ends of the bar for 20 sec, flipping and repeating.

The samples were stored submerged in distilled water at 37 deg. C. prior to testing (16 to 24 hrs). Flexural Strength and Flexural Modulus of the bars was measured on an Instron tester (Instron 4505 or Instron 1123, Instron Corp., Canton, Mass.) according to ANSI/ADA (American National Standard/American Dental Association) specification No. 27 (1993) at a crosshead speed of 0.75 mm/minute. The results were reported in megapascals (MPa).

Compressive Strength Test Method

Compressive strength of a test sample was measured according to the following procedure. An uncured composite sample was injected into a 4-mm (inside diameter) glass tube; the tube was capped with silicone rubber plugs; and then the tube was compressed axially at approximately 2.88 kg/cm² pressure for 5 minutes. The sample was then light cured for 80 seconds by exposure to a XL 1500 dental curing light (3M Company, St. Paul, Minn.), followed by irradiation for 90 seconds in a Kulzer UniXS curing box (Heraeus Kulzer GmbH, Germany). Cured samples-were cut with a diamond saw to form 8-mm long cylindrical plugs for measurement of compressive strength. The plugs were stored in distilled water at 37° C. for about 24 hours prior to testing. Measurements were carried out on an Instron tester (Instron 4505, Instron Corp., Canton, Mass.) with a 10 kilonewton (kN) load cell at a crosshead speed of 1 mm/minute according to ISO Specification 7489 (or American Dental Association (ADA) Specification No. 27). Cured samples were prepared and measured with the results reported in MPa as the average of multiple measurements.

The components shown in the tables were measured and mixed together until uniform.

|   | TTEO-IEM | Isocyanurate Trimer | TTEO-MA | CPQ | EDMAB | DPIHFP | Zr/Si Filler | AFM-1 | AFM-2 | AFM wt % of resin only |
|---|---|---|---|---|---|---|---|---|---|---|
| CE1 | 9.599 | 9.655 | 1.951 | 0.037 | 0.209 | 0.108 | 78.44 | | | |
| 101 | 9.547 | 9.54 | 1.915 | 0.035 | 0.211 | 0.106 | 78.43 | 0.21 | | 0.99 |
| 102 | 9.422 | 9.383 | 1.89 | 0.039 | 0.207 | 0.104 | 78.42 | 0.54 | | 2.48 |
| 103 | 9.161 | 9.204 | 1.817 | 0.032 | 0.203 | 0.101 | 78.42 | 1.06 | | 4.91 |
| 104 | 8.947 | 8.921 | 1.789 | 0.032 | 0.196 | 0.101 | 78.42 | 1.59 | | 7.371 |
| CE2 | 9.995 | 10.162 | 1.055 | 0.032 | 0.216 | 0.11 | 78.43 | | | |
| 105 | 9.922 | 10.052 | 1.034 | 0.037 | 0.214 | 0.106 | 78.42 | | 0.21 | 0.99 |
| 106 | 9.777 | 9.9 | 1.003 | 0.037 | 0.207 | 0.106 | 78.44 | | 0.53 | 2.46 |
| 107 | 9.517 | 9.622 | 1.022 | 0.032 | 0.203 | 0.101 | 78.43 | | 1.07 | 4.97 |
| 108 | 9.269 | 9.383 | 0.989 | 0.037 | 0.198 | 0.099 | 78.43 | | 1.6 | 7.409 |

|   | TTEO-IEM | Isocyanurate Trimer | TTEO-MA | CPQ | EDMAB | DPIHFP | Zr/Si Filler | AFM-3 | AFM-4 | AFM wt % of resin only |
|---|---|---|---|---|---|---|---|---|---|---|
| CE3 | 9.925 | 10.063 | 1.039 | 0.032 | 0.181 | 0.092 | 78.67 | | | |
| 109 | 9.822 | 9.959 | 1.028 | 0.032 | 0.179 | 0.09 | 78.68 | 0.21 | | 0.98 |
| 110 | 9.659 | 9.796 | 1.011 | 0.03 | 0.177 | 0.087 | 78.71 | 0.53 | | 2.48 |
| 111 | 9.425 | 9.558 | 0.987 | 0.03 | 0.173 | 0.085 | 78.69 | 1.05 | | 4.93 |
| 112 | 9.195 | 9.323 | 0.962 | 0.03 | 0.169 | 0.083 | 78.66 | 1.58 | | 7.39 |
| CE4 | 9.907 | 10.043 | 1.055 | 0.036 | 0.209 | 0.109 | 78.64 | | | |
| 113 | 9.806 | 9.943 | 1.045 | 0.038 | 0.211 | 0.105 | 78.64 | | 0.21 | 0.98 |
| 114 | 9.661 | 9.794 | 1.027 | 0.038 | 0.205 | 0.109 | 78.64 | | 0.52 | 2.45 |
| 115 | 9.409 | 9.539 | 1.002 | 0.038 | 0.216 | 0.105 | 78.64 | | 1.05 | 4.92 |
| 116 | 9.166 | 9.292 | 0.976 | 0.034 | 0.209 | 0.107 | 78.64 | | 1.58 | 7.38 |

|   | TGP-IEM | Isocyanurate Trimer | TTEO-MA | CPQ | EDMAB | DPIHFP | Zr/Si Filler | AFM-1 | AFM wt % of resin only |
|---|---|---|---|---|---|---|---|---|---|
| CE5 | 9.6 | 9.655 | 1.951 | 0.037 | 0.209 | 0.108 | 78.44 | | |
| 117 | 9.55 | 9.54 | 1.915 | 0.035 | 0.211 | 0.106 | 78.43 | 0.21 | 0.99 |
| 118 | 9.42 | 9.383 | 1.89 | 0.039 | 0.207 | 0.104 | 78.42 | 0.54 | 2.48 |
| 119 | 9.16 | 9.204 | 1.817 | 0.032 | 0.203 | 0.101 | 78.42 | 1.06 | 4.91 |
| 120 | 8.95 | 8.921 | 1.789 | 0.032 | 0.196 | 0.101 | 78.42 | 1.59 | 7.371 |

The test results are reported as follows. For each test the average is reported followed by the standard deviation in parenthesis. The number of samples utilized for each test is reported in the first row as "n". Thus, n=3 means three samples were tested.

|   | Stress, um deflection (n = 3) | Watts shrinkage, negative % (n = 5) | Diametral tensile strength, MPa (n = 6) | Barcol hardness, 2.5 mm, top (n = 6) | Barcol hardness, 2.5 mm, bottom (n = 6) | Barcol hardness, 4.0 mm, top (n = 6) | Barcol hardness, 4.0 mm, bottom (n = 6) | Depth of Cure, mm (n = 3) |
|---|---|---|---|---|---|---|---|---|
| CE1 | 2.01 (0.11) | 1.51 (0.04) | 87.8 (5.2) | 67.5 (2.5) | 65.7 (2.1) | 67.7 (2.6) | 72.8 (1.6) | 5.04 (0.11) |
| 101 | 1.57 (0.14) | 1.50 (0.05) | 81.6 (3.9) | 66.3 (1.4) | 66.5 (2.6) | 66.8 (1.3) | 69.3 (1.2) | 4.84 (0.22) |
| 102 | 0.96 (0.04) | 1.19 (0.06) | 84.0 (7.8) | 40.5 (3.0) | 49.7 (5.0) | 50.7 (1.2) | 53.5 (3.0) | 4.43 (0.04) |
| 103 | 0.96 (0.02) | 1.15 (0.01) | 84.3 (3.0) | 41.5 (3.3) | 47.2 (3.0) | 50.7 (1.4) | 49.7 (0.8) | 4.29 (0.08) |
| 104 | 0.77 (0.05) | 1.15 (0.05) | 85.4 (7.7) | 43.5 (5.8) | 39.0 (5.9) | 46.8 (1.5) | 50.3 (3.4) | 4.21 (0.07) |
| CE2 | 2.02 (0.13) | 1.42 (0.04) | 88.3 (2.1) | 71.8 (0.8) | 66.5 (1.8) | 71.0 (1.1) | 68.5 (0.8) | 5.08 (0.03) |
| 105 | 1.76 (0.08) | 1.31 (0.02) | 89.2 (5.4) | 66.2 (0.8) | 67.3 (2.1) | 69.3 (0.8) | 68.5 (2.4) | 4.74 (0.09) |
| 106 | 1.50 (0.11) | 1.24 (0.05) | 86.2 (3.2) | 58.8 (1.7) | 64.0 (1.6) | 64.5 (1.1) | 65.3 (0.8) | 4.58 (0.05) |
| 107 | 0.86 (0.03) | 1.08 (0.04) | 81.7 (5.3) | 50.8 (1.5) | 53.5 (2.1) | 54.2 (1.8) | 56.2 (2.3) | 4.39 (0.05) |
| 108 | 0.54 (0.06) | 0.98 (0.04) | 79.2 (3.6) | 29.0 (7.1) | 36.3 (2.8) | 41.2 (1.5) | 44.3 (2.4) | 3.98 (0.11) |
| CE3 | 1.78 (0.16) | 1.39 (0.03) | 87.9 (12.7) | 66.7 (1.8) | 71.0 (1.6) | 69.5 (1.9) | 70.7 (1.2) | 4.55 (0.14) |
| 109 | 1.82 (0.12) | 1.35 (0.02) | 85.9 (8.3) | 64.7 (1.2) | 66.2 (1.9) | 66.0 (1.3) | 69.5 (1.1) | 4.50 (0.06) |
| 110 | 1.42 (0.17) | 1.31 (0.04) | 89.7 (6.7) | 61.0 (2.1) | 65.0 (0.9) | 66.5 (1.6) | 68.3 (1.4) | 4.35 (0.04) |
| 111 | 1.16 (0.06) | 1.21 (0.03) | 87.6 (9.3) | 54.5 (2.4) | 55.5 (1.9) | 59.0 (2.6) | 65.2 (1.5) | 3.96 (0.10) |
| 112 | 0.95 (0.04) | 1.14 (0.01) | 85.2 (16.9) | 49.0 (1.8) | 54.8 (0.8) | 54.3 (1.4) | 55.2 (2.3) | 3.80 (0.10) |
| CE4 | 1.71 (0.06) | 1.36 (0.02) | 76.9 (3.8) | 64.2 (0.8) | 69.7 (2.4) | 65.3 (1.2) | 70.0 (1.3) | 4.38 (0.06) |
| 113 | 1.68 (0.01) | 1.40 (0.07) | 82.7 (6.5) | 66.0 (1.4) | 69.3 (1.0) | 65.5 (1.1) | 68.7 (1.9) | 4.37 (0.12) |
| 114 | 1.44 (0.02) | 1.35 (0.01) | 84.3 (3.8) | 60.3 (1.5) | 67.8 (1.0) | 64.3 (1.0) | 65.7 (1.2) | 4.24 (0.15) |
| 115 | 0.98 (0.08) | 1.24 (0.04) | 84.1 (8.5) | 54.8 (2.5) | 58.5 (1.1) | 56.3 (2.7) | 59.8 (1.2) | 3.85 (0.00) |
| 116 | 0.88 (0.03) | 1.17 (0.02) | 78.2 (6.0) | 51.7 (0.8) | 54.3 (1.6) | 49.7 (1.8) | 55.3 (1.0) | 3.66 (0.04) |
| CE5 | 1.35 (0.17) | 1.28 (0.05) | 78.5 (3.2) | 65.3 (0.8) | 69.5 (2.3) | 66.5 (3.4) | 61.3 (3.7) | 4.70 (0.05) |
| 117 | 1.25 (0.15) | 1.24 (0.06) | 73.8 (6.5) | 64.7 (1.6) | 62.7 (2.0) | 59.2 (1.3) | 62.7 (1.6) | 4.62 (0.14) |

-continued

| | Stress, um deflection (n = 3) | Watts shrinkage, negative % (n = 5) | Diametral tensile strength, MPa (n = 6) | Barcol hardness, 2.5 mm, top (n = 6) | Barcol hardness, 2.5 mm, bottom (n = 6) | Barcol hardness, 4.0 mm, top (n = 6) | Barcol hardness, 4.0 mm, bottom (n = 6) | Depth of Cure, mm (n = 3) |
|---|---|---|---|---|---|---|---|---|
| 118 | 1.10 (0.16) | 1.17 (0.03) | 74.0 (6.6) | 57.7 (1.6) | 61.3 (1.2) | 57.3 (2.2) | 57.7 (2.0) | 4.35 (0.07) |
| 119 | 0.62 (0.08) | 1.05 (0.01) | 78.0 (3.1) | 51.8 (1.6) | 51.2 (4.6) | 53.7 (1.4) | 49.0 (4.1) | 4.19 (0.03) |
| 120 | 0.55 (0.09) | 1.03 (0.02) | 72.6 (6.8) | 53.2 (2.1) | 51.2 (1.7) | 44.3 (3.4) | 39.2 (5.4) | 4.10 (0.05) |

The test results show the improved properties of Examples 101-120, comprising addition fragmentation materials, in comparison to CE1-CE5 that lack the inclusion of an addition fragmentation material. In particular, as the concentration of addition fragmentation materials, increased the compositions exhibits reduced stress and reduced Watts Shrinkage while maintaining sufficient Diametral tensile strength, Barcol hardness and depth of cure.

Dental compositions were also prepared wherein an addition-fragmentation monomer was added to a conventional dental composition. Compositions CE6 and 121 also contained 0.108 of DFIHFP and 0.03 of BHT.

| | BisGMA | TEGDMA | UDMA | BisEMA6 | CPQ | EDMAB | BZT | AFM-1 | Zr/Si Nano-Cluster Filler | AFM wt % of resin only |
|---|---|---|---|---|---|---|---|---|---|---|
| CE6 | 5.161 | 1.175 | 7.226 | 7.226 | 0.04 | 0.215 | 0.32 | | 78.5 | |
| 121 | 4.774 | 1.089 | 6.684 | 6.684 | 0.04 | 0.215 | 0.32 | 1.61 | 78.5 | 7.73 |

The test results are reported as follows. For each test the average is reported followed by the standard deviation in parenthesis. The number of samples utilized for each test is reported in the first row as "n".

| | Stress, um deflection (n = 2) | Watts shrinkage, negative % (n = 5) | Diametral tensile strength, MPa (n = 4-6) | Barcol hardness, 2.5 mm, top (n = 6) | Barcol hardness, 2.5 mm, bottom (n = 6) | Depth of Cure, mm (n = 3) |
|---|---|---|---|---|---|---|
| CE6 | 4.08 (0.18) | 1.87 (0.04) | 75.9 (3.0) | 76.3 (1.4) | 78.8 (1.5) | 4.68 (0.10) |
| 121 | 2.91 (0.28) | 1.77 (0.04) | 71.2 (9.4) | 76.0 (2.6) | 73.7 (1.7) | 4.24 (0.05) |

What is claimed is:

1. A non-aqueous polymerizable composition comprising at least one free-radically polymerizable monomer, an initiator and an addition-fragmentation agent of the formula:

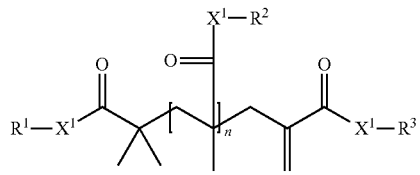

I wherein $R^1$, $R^2$ and $R^3$ are each independently $Z_m$-Q-, a (hetero)alkyl group or a (hetero)aryl group with the proviso that at least two of $R^1$, $R^2$ and $R^3$ is $Z_m$-Q-, Q is a linking group having a valence of m+1;

Z is an ethylenically unsaturated polymerizable group, m is 1 to 6;

each $X^1$ is independently —O— or —$NR^4$—, where $R^4$ is H or $C_1$-$C_4$ alkyl, and n is 0 or 1.

2. The polymerizable composition of claim 1 where Z comprises a vinyl, vinyloxy, (meth)acryloxy, (meth)acrylamido, styrenic and acetylenic functional groups.

3. The polymerizable composition of claim 1 where Z is selected from:

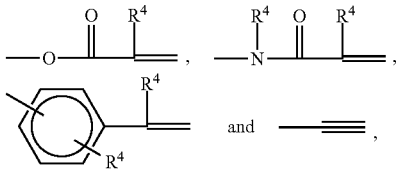

wherein $R^4$ is H or $C_1$-$C_4$ alkyl.

4. The polymerizable composition of claim 1 wherein Q is selected from
from —O—, —S—, —$NR^4$—, —$SO_2$—, —$PO_2$—, —CO—, —OCO—, —$R^6$—, —$NR^4$—CO—$NR^4$—, —$NR^4$—CO—O—, —$NR^4$—CO—$NR^4$—, —CO—O—$R^6$—, —CO—$NR^4$—$R^6$—, —$R^6$—CO—O—$R^6$—, —O—$R^6$—, —S—$R^6$—, —$NR^4$—$R^6$—, —$SO_2$—$R^6$—, —$PO_2$—$R^6$—, —CO—$R^6$—, —OCO—$R^6$—, —$NR^4$—CO—$R^6$—, and $NR^4$—$R^6$—

CO—O—, wherein each $R^4$ is hydrogen, a $C_1$ to $C_4$ alkyl group, or aryl group, each $R^6$ is an alkylene group having 1 to 6 carbon atoms, a 5- or 6-membered cycloalkylene group having 5 to 10 carbon atoms, or a divalent arylene group having 6 to 16 carbon atoms, with the proviso that Q-Z does not contain peroxidic linkages.

5. The polymerizable composition of claim 1 where Q is an alkylene.

6. The polymerizable composition of claim 5 wherein Q is an alkylene of the formula —$C_rH_{2r}$—, where r is 1 to 10.

7. The polymerizable composition of claim 1 where Q is a hydroxyl-substituted alkylene.

8. The polymerizable composition of claim 1 where Q is —$CH_2$—CH(OH)—$CH_2$—.

9. The polymerizable composition of claim 1 where Q is an aryloxy-substituted alkylene.

10. The polymerizable composition of claim 1 where $R^5$ is an alkoxy-substituted alkylene.

11. The polymerizable composition of claim 1 wherein $R^1$—$X^1$— groups and $R^3$—$X^1$— groups are selected from $H_2C$=$C(CH_3)C(O)$—O—$CH_2$—CH(OH)—$CH_2$—O—, $H_2C$=$C(CH_3)C(O)$—O—$CH_2$—CH(O—(O)C($CH_3$)=$CH_2$)—$CH_2$—O—, $H_2C$=$C(CH_3)C(O)$—O—CH($CH_2$OPh)-$CH_2$—O—, $H_2C$=$C(CH_3)C(O)$—O—$CH_2CH_2$—N(H)—C(O)—O—CH($CH_2$OPh)-$CH_2$—O—, $H_2C$=$C(CH_3)C(O)$—O—$CH_2$—CH(O—(O)C—N(H)—$CH_2CH_2$—O—(O)C($CH_3$)C=$CH_2$)—$CH_2$—O—, $H_2C$=C(H)C(O)—O—($CH_2$)$_4$—O—$CH_2$—CH(OH)—$CH_2$—O—, $H_2C$=$C(CH_3)C(O)$—O—$CH_2$—CH(O—(O)C—N(H)—$CH_2CH_2$—O—(O)C($CH_3$)C=$CH_2$)—$CH_2$—O—, $CH_3$—($CH_2$)$_7$—CH(O—(O)C—N(H)—$CH_2CH_2$—O—(O)C($CH_3$)C=$CH_2$)—$CH_2$—O—, $H_2C$=C(H)C(O)—O—($CH_2$)$_4$—O—$CH_2$—CH(—O—(O)C(H)=$CH_2$)—$CH_2$—O— and $H_2C$=C(H)C(O)—O—$CH_2$—CH(OH)—$CH_2$—O—.

12. The polymerizable composition of claim 1 comprising:
a) 85 to 100 parts by weight of an (meth)acrylic acid ester of non-tertiary alcohol;
b) 0 to 15 parts by weight of an acid functional ethylenically unsaturated monomer;
c) 0 to 10 parts by weight of a non-acid functional, ethylenically unsaturated polar monomer;
d) 0 to 5 parts vinyl monomer; and
e) 0 to 5 parts of a multifunctional (meth)acrylate;
based on 100 parts by weight total monomer, and
f) 0.1 to 10 parts by weight of the addition-fragmentation agent, based on 100 parts by weight of a) to e).

13. The polymerizable composition of claim 12 further comprising 0.01 to 5 parts of a multifunctional (meth) acrylate.

14. The polymerizable composition of claim 1 further comprising an organic solvent.

15. The polymerizable composition of claim 1 having less than 0.1 wt. % water.

16. An article comprising a layer of the polymerizable composition of claim 1 on a substrate.

17. An article comprising the cured polymerizable composition of claim 1 on a substrate.

18. A method of bonding two substrates together comprising the steps of coating the polymerizable composition of claim 1 to a surface of one or both substrates, contacting the coated surfaces, optionally with pressure, and curing the polymerizable composition.

19. A method of bonding two substrates together comprising the steps of coating the polymerizable composition of claim 1 to a surface of one or both substrates, wherein the coating of polymerizable composition is at least partially cured, contacting the coated surfaces optionally with pressure, and further curing the polymerizable compositions if necessary.

* * * * *